United States Patent [19]
Takenouchi et al.

[11] Patent Number: 5,945,450
[45] Date of Patent: Aug. 31, 1999

[54] NAPHTHALENE DERIVATIVE

[75] Inventors: Kazuya Takenouchi; Katsushi Takahashi; Masaichi Hasegawa; Takahiro Takeuchi, all of Hino; Keiji Komoriya, Tokyo, all of Japan

[73] Assignee: Teijin Limited, Osaka, Japan

[21] Appl. No.: 08/737,991

[22] PCT Filed: May 30, 1995

[86] PCT No.: PCT/JP95/01035

§ 371 Date: Nov. 22, 1996

§ 102(e) Date: Nov. 22, 1996

[87] PCT Pub. No.: WO95/32943

PCT Pub. Date: Dec. 7, 1995

[30] Foreign Application Priority Data

May 31, 1994 [JP] Japan .................................. 6-118267
Dec. 22, 1994 [JP] Japan .................................. 6-320261

[51] Int. Cl.[6] .......................... A61K 31/24; C07C 229/00
[52] U.S. Cl. ........................ 514/535; 514/381; 514/522; 514/533; 514/534; 514/561; 514/562; 514/563; 514/602; 514/603; 514/618; 514/619; 548/253; 558/415; 558/416; 560/17; 562/427; 562/455; 564/84; 564/85; 564/86; 564/88; 564/162; 564/168
[58] Field of Search ..................... 514/535, 533, 514/534, 561, 562, 563, 522, 381, 602, 603, 618, 619; 560/10, 21, 17, 43; 562/427, 455; 558/415, 416; 548/253; 564/84, 85, 86, 88, 162, 168

[56] References Cited

U.S. PATENT DOCUMENTS 3,264,378  8/1966  Dailey et al. .
4,990,650  2/1991  Hazato et al. ............... 560/48

FOREIGN PATENT DOCUMENTS

| 102325 | 1/1987 | European Pat. Off. . | |
| 60-116657 | 6/1985 | Japan | C07C 103/78 |
| 02218654 | 10/1988 | Japan . | |
| 63-270634 | 11/1988 | Japan . | |
| 1106818 | 4/1989 | Japan . | |
| 1287066 | 11/1989 | Japan . | |
| 2218654 | 8/1990 | Japan . | |
| WO 90 12001 | 10/1990 | Japan . | |
| 3215421 | 9/1991 | Japan . | |
| 3-258749 | 11/1991 | Japan | C07C 65/34 |
| 4290818 | 10/1992 | Japan . | |
| 5271068 | 10/1993 | Japan . | |

OTHER PUBLICATIONS

Department of Bacteriology, Department of Opthamology, School of Medicine, Iwate Medical University, Japan Opthalmol. Soc. 1993 pp. 792–799 Kazuhiro Takahashi, "Participation of Procoagulant Activity of Cultured Rabbit Lens Epithelial Cells in Fibrin Formulation".

*European Journal of Medicinal Chemistry*, vol. 26, Mar. 1991, pp. 159–166, Murray, et al. Novel 6–oxo–6–naphthylhexaonic acid derivatives with anti–inflammatory and 5–lipoxygenase Inhibitory Activity.

*Helvetica Chimica Acta*, vol. 39, (1956), pp. 1892–1899, Chardonnens et al. Sur l'aptitude reactionnelle du groupement methylique XIV), Influence des groupements α– et β–naphtoyles.

*Biochemical and Biophysical Research Communications*, vol. 119, Feb. 29, 1984, Crutchley, pp. 179–184 "Effects of Inhibitors of Arachidonic Acid Metabolism on Thromboplastin Activity in Human Monocytes".

Chardonnens et.al., Helv. Chim. Acta, vol. XXXIX, No. 224, pp. 1892–1899, 1956.

International Search Report.

*Primary Examiner*—Shailendra Kumar
*Attorney, Agent, or Firm*—Sughrue, Mion, Zinn, Macpeak & Seas, PLLC

[57] ABSTRACT

Naphthalene derivatives represented by formula [I]:

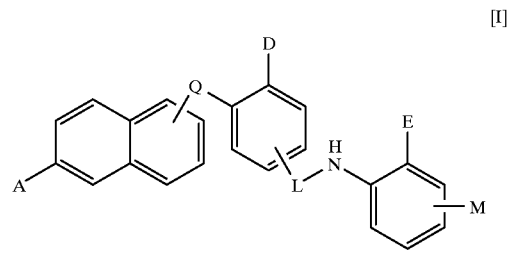

(wherein A is a hydrogen atom, a hydroxy group, a $C_7$–$C_{11}$ aralkyloxy group, or an alkoxy group composed of an oxy group and a $C_1$–$C_{12}$ aliphatic or alicyclic, saturated or unsaturated hydrocarbon group where the allyl may be substituted with a $C_6$–$C_{10}$ allyloxy group; Q represents O, S, $CH_2$, O—$CH_2$, S—$CH_2$, CO, or $CHOR^1$; L represents CO, $CR^2R^3CO$, $CH_2CH_2CO$, or CH=CHCO; D represents a hydrogen atom, $NO_2$, $NH_2$, $CO_2R^4$, or a group having the following formula [II]:

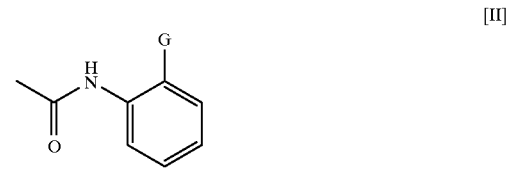

(wherein G represents. a hydrogen atom, OH, $SO_2NH_2$, $CO_2R^6$, CN, or a tetrazol-5-yl group); E represents a hydrogen atom, OH, $SO_2NH_2$, $CO_2R^5$, CN, or a tetrazol-5-yl group; M represents a hydrogen atom, a $C_1$–$C_4$ lower alkyl group, a nitro group, or a halogen atom; and $R^1$, $R^2$, $R^3$, $R^4$, $R^5$ and $R^6$ are, independently each other, a hydrogen atom or a $C_1$–$C_4$ lower alkyl group);

pharmacologically acceptable salts thereof, or pharmacologically acceptable solvates thereof, which have, for example, an inhibitory effect on the production of IgE antibodies, and will be useful for prophylaxis and/or treatment of allergic diseases.

24 Claims, No Drawings

NAPHTHALENE DERIVATIVE

This application is a 371 of PCT/JP95/01035, filed May 30, 1995.

TECHNICAL FIELD

The present invention relates to new naphthalene derivatives, their pharmacologically acceptable salts or their pharmacologically acceptable solvates, the pharmaceutical compositions containing them, and the application thereof as drugs. More particularly, the present invention relates to new naphthalene derivatives having a naphthalene moiety and two benzene moieties at the same time or their pharmacologically acceptable salts, or their pharmacologically acceptable solvates, the pharmaceutical compositions containing them, and the application thereof as drugs. Furthermore particularly, the present invention relates to the new naphthalene derivatives which, owing to a feature of inhibiting the production of IgE antibodies, is useful as a drug for prophylaxis and/or treatment of allergic diseases, or is useful as a drug for prophylaxis and/or treatment of the diseases caused by enhanced production or activity of TF (tissue factor), and their pharmacologically acceptable salts, or their pharmacologically acceptable solvates.

BACKGROUND ART

It has been known that various chemical mediators released from mast cells are deeply involved in the production of allergic diseases represented by asthma and atopic dermatitis, and that the allergic reaction arises as a result of binding of the Fc region of IgE antibodies with their receptors on the membranes of those cells. Indeed, it has been also known that the serum or tissue concentration of IgE antibodies of the patient with an allergic disease is considerably higher an than that of normal persons. Furthermore, the patient with an allergic disease has been known to show a maintained production of interleukin 4 (IL-4) which plays an important role in the production of IgE antibodies. Accordingly, if a drug were discovered that could inhibit the production of IgE antibodies, it would be effective for prophylaxis and/or treatment of allergic diseases. However, what is now used for the treatment of allergic diseases mainly consists of drugs blocking the receptor of histamine which is one of chemical mediators, or drugs suppressing the release of chemical mediators from their productive cells, and drugs that might inhibit the production of IgE antibodies have never been used for the treatment of allergic diseases. If a new drug were discovered that could inhibit the production of IgE antibodies, it would be useful as a more fundamental drug for prophylaxis and/or treatment of allergic diseases, because it would intercept allergic reactions at an earlier stage than is possible with the conventional drugs that interfere with the release of chemical mediators from their productive cells.

TF (tissue factor) is a complex composed of lipids and glycoproteins localized in the membrane fraction from tissues and cells, and recognized widely over the living body especially in brain, lungs, placenta, kidneys, etc. In addition, vascular endothelial cells, monocytes and/or macrophages, when stimulated from outside, are induced to produce TF, and express it on the surface of their cell membranes.

This TF is practically an initiator of extrinsic coagulation pathway, and is deeply involved in hemostasis/coagulation. More precisely, TF forms a complex with factor VII to activate factor VII, and the resulting TF-VIIa complex contributes to the activation of factors IX and X. Further, because TF is expressed/produced by macrophages as mentioned above, it has been thought that it is involved in biophylaxis including the immune system.

When a tissue is injured in trauma, burns, a variety of operations, or in lesions such as malignant tumors, fulminant hepatitis, sepsis and the like, TF is released into blood stream, which may activate the extrinsic coagulation pathway so much as to cause various disorders. DIC (disseminated intravascular coagulation) is known as one of such disorders. Further, during infection, delayed immune response, various rejection reactions subsequent to tissue transplantation, glomerular nephritis, viral hepatitis, etc., production of TF in vascular endothelial cells, monocytes, and/or macrophages is enhanced to cause thrombosis. Furthermore, thrombin which is located downstream of the extrinsic coagulation pathway can also act as a stimulant of proliferation of smooth muscles. Therefore, increased activity of TF may result in diseases related with thickened endothelium such as arteriosclerosis or restenosis.

Even if an injury is inflicted on an avascular tissue, it causes enhanced production of TF in the affected cells, which may lead to various disorders. One of such disorders is opacification after the insertion of an artificial crystalline lens for the treatment of cataract (Japanese Patent TOKKAIHEI (Unexamined) No. 5-271068 and Takahashi, J. Jap. Opthalmol. Soc., 97:792–799, 1993).

From above it is obvious that if a drug were found that could suppress the production or activity of TF, it would be also quite effective for prophylaxis/treatment of the disorders closely related with enhanced production/activity of TF.

Prior arts related with the compounds of this invention include the following.

Japanese Patent TOKKAIHEI (Unexamined) No. 1-287066 showed that the compound having a naphthalene moiety and an anthranilic acid moiety at the same time such as N-(2-naphthoyl) anthranilic acid has an antiallergic activity or an inhibitory activity of 5-lipoxygenase. However, the compound described in this reference is characterized with a structure wherein a two-ring aromatic derivative which has been substituted with hydroxy or alkoxy groups is directly combined with an anthranilic acid moiety via amide bond. Further, the reference did not mention anything whether the compound has an inhibitory effect on the production of IgE antibodies.

Similarly, Japanese Patent TOKKAISHO (Unexamined) No. 63-270634 demonstrated that the compound which has a naphthalene moiety and an anthranilic acid moiety at the same time can inhibit the activity of lipoxygenase and have an anti-SRS-A activity. However, in the compound described above, a naphthalene moiety is connected to an anthranilic acid moiety via an alkyl aliphatic. Further, the reference gave no mention whether the compound inhibits the production of IgE antibodies.

Furthermore, Japanese Patent TOKKAIHEI (Unexamined) No. 1-106818 and PCT WO 90/12001 describes the compound having a naphthalene moiety is capable of suppressing allergy reactions and of inhibiting the production of IgE antibodies. However, those compounds described in the two references have the following characteristics: the former must have a cyclopropane structure, and the latter must have substitutable groups in the naphthalene ring such as hydroxy groups.

According to an article (Eur. J. Med. Chem. 26:159–166 (1991)), it was reported that a group of compounds having naphthalene moiety is capable of inhibiting the activity of lipoxygenase, and that a certain compound comprising a naphthalene moiety and a 2-hydroxyaniline amide structure is mentioned. However, in this compound, a naphthalene moiety is connected to a 2-hydroxyaniline amide structure via an alkyl aliphatic. Furthermore, that article gave no mention whether the compound has an inhibitory effect on the production of IgE antibodies.

Further, in EP-102325-A, there was a description of a compound wherein a benzene moiety is linked via a sulfone group to a naphthalene moiety, and to the benzene moiety another benzene moiety is linked via amide bond. However, the present specification described herein did not disclose the compound where a naphthalene moiety was linked to a benzene moiety via a sulfone group. Further the latter benzene moiety linked to the former benzene via amide has a sulfonic acid substituent. Therefore, the compound in question is obviously different from the compound in this invention. Furthermore, the reference does not give any mention about inhibitory effects of that compound on the production of IgE antibodies.

In another article (Helv. Chem. Acta 39:1892–1899 (1956)), it was reported a compound where a benzene moiety was linked to a naphthalene moiety via a carbonyl group, and then another benzene was linked to above benzene moiety via amide bond. However, as regards the compound described in this article, the former benzene moiety linked to the naphthalene moiety via a carbonyl group has a nitro substituent at the meta-position of the carbonyl group, and the second benzene moiety linked to above benzene moiety via amide bond has a dimethylamino substituent. In short, the compound in the article is obviously different from the compound in this invention is going to present. Further, the article did not mention any inhibitory effects of the compound on the production of IgE antibodies.

Furthermore, neither articles nor references mentioned heretofore described whether the compounds have any inhibitory effects on TF activities.

Japanese Patents TOKKAIHEI Nos. 3-215421 and 5-271068 disclosed that certain compounds interfere with the activity of TF. However, these compounds have a naphthalene moiety, a cyclopropane moiety, and an anthranilic acid moiety at the same time, thus being quite different in structure from the compound this invention is going to present.

It has been known that the compounds interfering with the activity of TF include Vitamin A (Horie et al., Japanese Patent TOKKAIHEI No. 4-290818), phospholipid derivatives (U.S. Pat. No. 3,264,378), and $PLA_2$ inhibitors such as 4-bromophenacyl bromide or quinacrine (BBRC 119:179–184, (1984)). However, these compounds have no similarities in their structure to the compound this invention is going to present.

With these prior arts as a background, the present inventors had studied to provide new naphthalene derivatives useful as a pharmaceutical product, and succeeded in providing the compounds of this invention.

DISCLOSURE OF THE INVENTION

The present invention provides naphthalene derivatives having the following formula [I]:

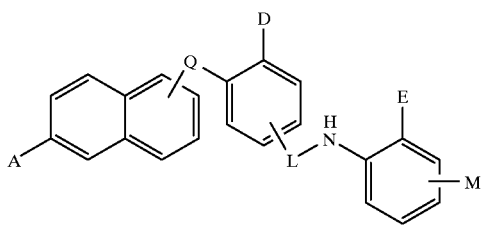

(wherein A represents a hydrogen atom, a hydroxy group, a $C_7$–$C_{11}$ aralkyl oxy group, or an alkoxy group composed of an oxy group and a $C_1$–$C_{12}$ aliphatic or alicyclic, saturated or unsaturated hydrocarbon group where the alkyl may be substituted with a $C_6$–$C_{10}$ aryloxy group; Q represents O, S, $CH_2$, O—$CH_2$, S—$CH_2$, CO, or $CHOR^1$; L represents CO, $CR^2R^3CO$, $CH_2CH_2CO$, or CH=CHCO; D represents a hydrogen atom, $NO_2$, $NH_2$, $CO_2R^4$, or a group having the following formula [II]:

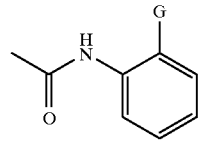

(wherein G represents a hydrogen atom, OH, $SO_2NH_2$, $CO_2R^6$, CN, or a tetrazol-5-yl group); E represents a hydrogen atom, OH, $SO_2NH_2$, $CO_2R^5$, CN, or a tetrazol-5-yl group; M represents a hydrogen atom, a $C_1$–$C_4$ lower alkyl group, a nitro group, or a halogen atom; and $R^1$, $R^2$, $R^3$, $R^4$, $R^5$ and $R^6$, independently each other, represent a hydrogen atom or a $C_1$–$C_4$ lower alkyl group); pharmacologically acceptable salts thereof and pharmacologically acceptable solvates thereof; pharmaceutical compositions comprising the naphthalene derivatives, pharmacologically acceptable salts thereof, or pharmacologically acceptable solvates thereof as an active ingredient and a pharmaceutically acceptable carrier; drugs effective for propylaxis and/or treatment of allergic diseases, comprising the naphthalene derivatives, pharmacologically acceptable salts thereof, or pharmacologically acceptable solvates thereof as an active ingredient, and characterized by having an inhibitory activity on the production of IgE antibodies; and drugs effective for propylaxis and/or treatment of diseases caused by enhanced production or activity of TF, comprising the naphthalene derivatives, pharmacologically acceptable salts thereof, or pharmacologically acceptable solvates thereof as an active ingredient.

BEST EMBODIMENT OF THE INVENTION

In formula [I], M represents a hydrogen atom, a $C_1$–$C_4$ lower alkyl group, a nitro group or a halogen atom. The lower alkyl group includes methyl, ethyl, (n-, i-) propyl and (n-, i-, t-) butyl group, and the halogen atom includes fluorine, chlorine and bromine atoms. Among these, hydrogen atom, methyl group, ethyl group, nitro group, fluorine atom or chlorine atom is preferred as F, particularly hydrogen atom is most preferred.

In formula [I], E represents OH, $SO_2NH_2$, $CO_2R^5$, CN or a tetrazol-5-yl group. Among these, $CO_2R^5$ or a tetrazol-5-yl is preferred as E. Here $R^5$ represents a hydrogen atom or a $C_1$–$C_4$ lower alkyl group. The lower alkyl group includes methyl, ethyl, (n-, i-) propyl and (n-, i-, t-) butyl group. Among these, hydrogen atom, a methyl group or ethyl group is particularly preferred as $R^5$.

In formula [I], D represents a hydrogen atom, $NO_2$, $NH_2$, $CO_2R^4$ ($R^4$ represents a hydrogen atom or a $C_1$–$C_4$ lower alkyl group), or a group represented by formula [II] (where G represents a hydrogen atom, OH, $SO_2NH_2$, $CO_2R^6$ ($R^6$ represents a hydrogen atom or a $C_1$–$C_4$ lower alkyl group), CN, or a tetrazol-5-yl group). Among these, a hydrogen atom, $NO_2$, $NH_2$, or the group represented by formula [II] is preferred as D. As G, a hydrogen atom or $CO_2R^6$ is preferred. Further, $R^4$ and $R^6$ independently represent a hydrogen atom or a $C_1$–$C_4$ lower alkyl group. The lower alkyl group includes methyl, ethyl, (n-, i-) propyl and a (n-, i-, t-) butyl group. As $R^4$ and $R^6$, independently each other, a hydrogen atom, a methyl group or ethyl group is preferably mentioned.

In formula [I], A represents a hydrogen atom, a hydroxy group, a $C_7$–$C_{11}$ aralkyl oxy group, or an alkoxy group composed of an oxy group and a $C_1$–$C_{12}$ aliphatic or alicyclic, saturated or unsaturated hydrocarbon group where the alkyl may be substituted with a $C_6$–$C_{10}$ aryloxy group.

The compounds represented by A include, for example, hydrogen atom, hydroxy group, methoxy group, ethoxy group, (n-, i-) propyloxy group, (n-, i-, t-) butoxy group, n-pentyloxy group, n-hexyloxy group, n-octyloxy group, n-decyloxy group, n-dodecyloxy group, cyclopropyloxy group, cyclopropylmethyloxy group, cyclobutyloxy group, cyclopentyloxy group, cyclohexyloxy group, allyloxy group, crotyloxy group, 3-butenyloxy group, 4-pentenyloxy group, 5-hexenyloxy group, 7-octenyloxy group, geranyloxy group, 2-phenoxyethoxy group, 3-phenoxypropyloxy group, 4-phenoxybutoxy group, benzyloxy group, 2-phenylethoxy group, 3-phenylpropyloxy group, 1-naphtylmethyloxy group, 2-naphtylmethyloxy group, etc. Among these, a hydrogen atom; a hydroxy group; a benzyloxy group, a phenylpropyloxy group, or a naphtylmethyloxy group; or an alkoxy group composed of an oxy group and a $C_1$–$C_{12}$ aliphatic or alicyclic saturated hydrocarbon group where the alkyl may be substituted by a phenyloxy group or an alkoxy group composed of an oxy group and a $C_3$–$C_{10}$ aliphatic unsaturated hydrocarbon group; such as hydrogen atom, hydroxy group, methoxy group, ethoxy group, (n-, i-) propyloxy group, (n-, i-, t-) butoxy group, n-hexyloxy group, n-octyloxy group, n-decyloxy group, n-dodecyloxy group, cyclopropylmethyloxy group, cyclohexyloxy group, allyloxy group, 4-pentenyloxy group, geranyloxy group, 4-phenoxybutoxy group, benzyloxy group, 3-phenylpropyloxy group, 1- naphtylmethyloxy group, 2-naphtylmethyloxy group can be mentioned as preferred compounds. More specifically, a hydrogen atom; a hydroxy group; an alkoxy group composed of an oxy group and a $C_1$–$C_8$ aliphatic or alicyclic saturated hydrocarbon group which can be substituted by a phenyloxy group such as methoxy group, t-butoxy group, n-octyloxy group, 4-phenoxybutoxy group, cyclohexyloxy group; or an alkoxy group composed of an oxy group and a $C_3$–$C_{10}$ aliphatic unsaturated hydrocarbon group such as allyloxy group, 4-pentenyloxy group, or geranyloxy group; benzyloxy group, 3-phenylpropyloxy group, or 2-naphtylmethyloxy group is most preferred.

In formula [I], Q represents O, S, $CH_2$, O—$CH_2$, S—$CH_2$, CO or $CHOR^1$ ($R^1$ represents a hydrogen atom or a $C_1$–$C_4$ lower alkyl group). Among these, Q should preferably be O, S, $CH_2$, O—$CH_2$, S—$CH_2$, or $CHOR^1$. More specifically, O, S, $CH_2$ or $CHOR^1$ is preferred, and O is preferred best of all. $R^1$ represents a hydrogen atom or a $C_1$–$C_4$ lower alkyl group. The lower alkyl group includes methyl group, ethyl group, (n-, i-) propyl group, (n-, i-, t-) butyl group, etc. Among these, hydrogen atom, methyl group or ethyl group should be preferred as $R^1$.

In formula [I], L represents CO, $CR^2R^3CO$ ($R^2$ and $R^3$ are hydrogen atom or $C_1$–$C_4$ lower alkyl group independently from each other), $CH_2CH_2CO$, or CH=CHCO. Among these, CO, $CR^2R^3CO$ or CH=CHCO is preferred as L. Particularly, CO or $CR^2R^3CO$ are preferred.

In preferred embodiments, $R^2$ and $R^3$ independently each other represent hydrogen atom or $C_1$–$C_4$ lower alkyl group. The lower alkyl group includes methyl group, ethyl group, (n-, i-) propyl group, (n-, i-, t-) butyl group, etc., and among these, hydrogen atom, methyl group, or ethyl group is preferred independently as $R^2$ and $R^3$. In the best preferred combinations, both $R^2$ and $R^3$ represent hydrogen atom, or in preferred combinations one of them consists of hydrogen atom and the other of $C_1$–$C_4$ lower alkyl group (particularly methyl or ethyl group).

In formula [I], the preferred combinations of E and D include $CO_2R^5$ or tetrazol-5-yl group as E, and hydrogen atom, $NO_2$, $NH_2$, or a group represented by formula [II] as D. Among these, a combination of $CO_2R^5$ as E, and hydrogen atom or $NO_2$ as D is preferred. In these cases, $R^5$ represents hydrogen atom or $C_1$–$C_4$ lower alkyl group, particularly hydrogen atom, methyl group or ethyl group. As for the groups included in formula [II], G represents a hydrogen atom or $CO_2R^6$, and $R^6$ represents a hydrogen atom or a $C_1$–$C_4$ lower alkyl group, particularly a hydrogen atom, a methyl group or ethyl group.

In formula [I], the preferred combinations of Q and L include:

(1) O, S, $CH_2$, O—$CH_2$, S—$CH_2$ or $CHOR^1$ as Q, and CO, $CR^2R^3CO$ or CH=CHCO as L;

(2) O, S, $CH_2$, or $CHOR^1$ as Q, and CO or $CR^2R^3CO$ as L;

(3) O as Q, and CO or $CR^2R^3CO$ as L;

(4) O, S, $CH_2$, O—$CH_2$, or S—$CH_2$ as Q, and CO as L;

(5) O as Q, and CH=CHCO as L.

When the combination (1), (2) or (3) is chosen, $R^1$, $R^2$ and $R^3$ represent independently hydrogen atom or $C_1$–$C_4$ lower alkyl group, particularly hydrogen atom, methyl group or ethyl group.

In formula [I], Q in the naphthalene ring is substituted at 1- or 2-position of the naphthalene ring, and preferably at the 2-position.

In formula [I] wherein the benzene ring has been substituted by Q, L and D, the relative position of Q and L may be ortho, meta or para, preferably para.

Naphthalene derivatives of this invention can be converted into pharmacologically acceptable solvates. The appropriate solvent includes water, methanol, ethanol, (n-, i-) propyl alcohol, (n-, t-) butanol, acetonitrile, acetone, methyl ethyl ketone, chloroform, ethyl acetate, diethyl ether, t-butyl methyl ether, benzene, toluene, DMF, DMSO, etc. Particularly, water, methanol, ethanol, (n-, i-)propyl alcohol and acetonitrile can be mentioned as preferred solvents.

In formula [I], when D represents $CO_2R^4$ wherein $R^4$ represents hydrogen atom; when E represents $CO_2R^5$ wherein $R^5$ is hydrogen atom; when G represents $CO_2R^6$ wherein $R^6$ is a hydrogen atom; when E represents a tetrazol-5-yl group; or when G represents a tetrazol-5-yl group, the naphthalene derivative of this invention can be converted into pharmacologically acceptable, non-toxic cationic salts or their solvates if it is necessary. Such salts include salts combined with: alkali metal ions such as $Na^+$, $K^+$, etc.; alkali earth metal ions such as $Mg^{2+}$, $Ca^{2+}$, etc.; metal ions such as $Al^{3+}$, $Zn^{2+}$, etc.; organic base compounds ammonia, triethylamine, ethylenediamine, propanediamine, pyrrolidine, piperidine, piperazine, pyridine, lysine, choline, ethanolamine, N,N-dimethylethanolamine, 4-hydroxypiperidine, glucosamine, N-methylglucamine, etc. Among these, $Na^+$, $Ca^{2+}$, lysine, choline, N,N-dimethylethanolamine, N-methylglucamine are preferred. The appropriate solvent required for their solvates includes water, methanol, ethanol, (n-, i-)propyl alcohol, (n-, t-)butanol, acetonitrile, acetone, methyl ethyl ketone, chloroform, ethyl acetate, diethyl ether, t-butyl methyl ether, benzene, toluene, DMF, DMSO, etc. Among these, water, methanol, ethanol, (n-, i-)propyl alcohol and acetonitrile can be mentioned as preferred solvents.

In formula [I], when D represents $NH_2$, the naphthalene derivative of this invention can be converted into pharmacologically acceptable acid salts or their solvates if it is necessary. Such acids include mineral acids such as hydrochloric acid, sulfuric acid, nitric acid, etc., or organic acids such as acetic acid, benzoic acid, fumaric acid, maleic acid, methanesulfonic acid, toluenesulfonic acid, etc. Among these, hydrochloric acid, sulfuric acid, acetic acid, fumaric acid, maleic acid, methanesulfonic acid, toluenesulfonic acid can be mentioned as preferred acids. Further, the solvents required for their solvates include water, methanol, (n-, i-) propyl alcohol, (n-, t-) buthanol, acetonitrile, acetone, methyl ethyl ketone, chloroform, ethyl acetate, diethyl ether, t-butyl methyl ether, benzene, toluene, DMF, DMSO, etc. Particularly, water, methanol, ethanol, (n-, i-)propyl alcohol, and acetonitrile can be mentioned as preferred solvents.

Preferred examples of naphthalene derivatives of this invention represented by formula [I] are the compounds listed in Tables 1-1 to 1-18; their solvates of water, methanol, ethanol, (n-, i-) propyl alcohol, or acetonitrile; their salts of sodium, potassium, lysine, choline, N,N-dimethylethanol amine, N-methylglucamine, hydrochloric acid, sulfuric acid, acetic acid, fumaric acid, maleic acid, methanesulfonic acid, and toluenesulfonic acid; and the solvates of their salts of water, methanol, ethanol, (n-, i-)propyl alcohol, or acetonitrile. For a compound that has an asymmetric carbon atom(s) in its structure, all the optical isomers should be included in the compounds of this invention, and for a compound that has a carbon-carbon double bond(s) in its structure, all the geometrical isomers should be included. "tet" in Tables 1-1, 1-2, 1-15 and 1-16 represents tetrazol-5-yl group.

TABLE 1-1

(A = H, M = H)

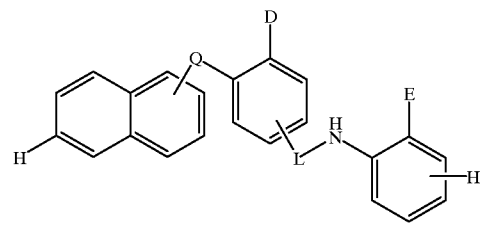

| Compound No. | Q | L | D | E | Substituted Position on Naphthalene*[1] | Substituted Position on Benzene*[2] |
| --- | --- | --- | --- | --- | --- | --- |
| 1101 | 0 | CO | H | $CO_2$ Me | 2-position | para |
| 1102 | 0 | CO | H | $CO_2$ Et | 2-position | para |
| 1103 | 0 | CO | H | $CO_2$ tBu | 2-position | para |
| 1104 | 0 | CO | H | $CO_2$ H | 2-position | para |
| 1105 | 0 | CO | H | H | 2-position | para |
| 1106 | 0 | CO | H | OH | 2-position | para |
| 1107 | 0 | CO | H | $SO_2 NH_2$ | 2-position | para |
| 1108 | 0 | CO | H | CN | 2-position | para |
| 1109 | 0 | CO | H | tet | 2-position | para |
| 1110 | 0 | CO | H | $CO_2$ Me | 1-position | para |
| 1111 | 0 | CO | H | $CO_2$ H | 1-position | para |
| 1112 | 0 | CO | H | $CO_2$ Me | 2-position | meta |
| 1113 | 0 | CO | H | $CO_2$ H | 2-position | meta |
| 1114 | 0 | CO | $NO_2$ | $CO_2$ Me | 2-position | para |
| 1115 | 0 | CO | $NO_2$ | $CO_2$ Et | 2-position | para |
| 1116 | 0 | CO | $NO_2$ | $CO_2$ H | 2-position | para |
| 1117 | 0 | CO | $NH_2$ | $CO_2$ Me | 2-position | para |
| 1118 | 0 | CO | $NH_2$ | $CO_2$ H | 2-position | para |
| 1119 | 0 | CO | $CO_2$ Me | $CO_2$ Me | 2-position | para |
| 1120 | 0 | CO | $CO_2$ H | $CO_2$ H | 2-position | para |
| 1121 | 0 | CO | [II], G = $CO_2$ Me | $CO_2$ Me | 2-position | para |
| 1122 | 0 | CO | [II], G = $CO_2$ H | $CO_2$ H | 2-position | para |

*[1])Position substituted by Q on naphthalene ring
*[2])Relative position of Q and L on the benzene ring that has been substituted by Q, L and D

TABLE 1-2

(A = H, M = H)

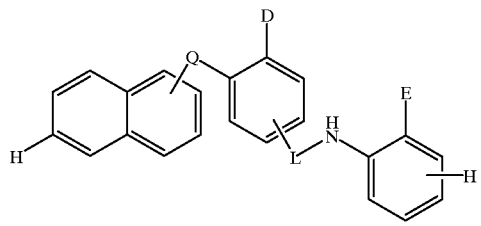

| Compound No. | Q | L | D | E | Substituted Position on Naphthalene[1] | Substituted Position on Benzene[2] |
|---|---|---|---|---|---|---|
| 1123 | O | $CH_2$ CO | H | $CO_2$ Me | 2-position | para |
| 1124 | O | $CH_2$ CO | H | $CO_2$ Et | 2-position | para |
| 1125 | O | $CH_2$ CO | H | $CO_2$ tBu | 2-position | para |
| 1126 | O | $CH_2$ CO | H | $CO_2$ H | 2-position | para |
| 1127 | O | $CH_2$ CO | H | H | 2-position | para |
| 1128 | O | $CH_2$ CO | H | OH | 2-position | para |
| 1129 | O | $CH_2$ CO | H | $SO_2$ $NH_2$ | 2-position | para |
| 1130 | O | $CH_2$ CO | H | CN | 2-position | para |
| 1131 | O | $CH_2$ CO | H | tet | 2-position | para |
| 1132 | O | $CH_2$ CO | H | $CO_2$ Me | 1-position | para |
| 1133 | O | $CH_2$ CO | H | $CO_2$ H | 1-position | para |
| 1134 | O | $CH_2$ CO | H | $CO_2$ Me | 2-position | meta |
| 1135 | O | $CH_2$ CO | H | $CO_2$ H | 2-position | meta |
| 1136 | O | $CH_2$ CO | $NO_2$ | $CO_2$ Me | 2-position | para |
| 1137 | O | $CH_2$ CO | $NO_2$ | $CO_2$ Et | 2-position | para |
| 1138 | O | $CH_2$ CO | $NO_2$ | $CO_2$ H | 2-position | para |
| 1139 | O | $CH_2$ CO | $NH_2$ | $CO_2$ Me | 2-position | para |
| 1140 | O | $CH_2$ CO | $NH_2$ | $CO_2$ H | 2-position | para |
| 1141 | O | $CH_2$ CO | $CO_2$ Me | $CO_2$ Me | 2-position | para |
| 1142 | O | $CH_2$ CO | $CO_2$ H | $CO_2$ H | 2-position | para |
| 1143 | O | $CH_2$ CO | [II], G = $CO_2$ Me | $CO_2$ Me | 2-position | para |
| 1144 | O | $CH_2$ CO | [II], G = $CO_2$ H | $CO_2$ H | 2-position | para |
| 1145 | O | $CH_2$ $CH_2$ CO | H | $CO_2$ Me | 2-position | para |
| 1146 | O | $CH_2$ $CH_2$ CO | H | $CO_2$ H | 2-position | para |
| 1147 | O | CH=CHCO | H | $CO_2$ Me | 2-position | para |
| 1148 | O | CH=CHCO | H | $CO_2$ H | 2-position | para |

[1] Position substituted by Q on naphthalene ring
[2] Relative position of Q and L on the benzene ring that has been substituted by Q, L, and D

TABLE 1-3

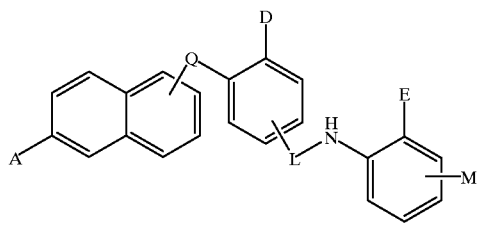

| Compound No | A | Q | L | D | E | M | Substituted Position on Naphthalene[1] | Substituted Position on Benzene[2] |
|---|---|---|---|---|---|---|---|---|
| 1201 | HO | O | CO | H | $CO_2$ Me | H | 2-position | para |
| 1202 | HO | O | CO | H | $CO_2$ H | H | 2-position | para |
| 1203 | MeO | O | CO | H | $CO_2$ Me | H | 2-position | para |
| 1204 | MeO | O | CO | H | $CO_2$ H | H | 2-position | para |
| 1205 | PhCH$_2$O | O | CO | H | $CO_2$ Me | H | 2-position | para |

TABLE 1-3-continued

[Structure: naphthalene (with A substituent) — O(Q) — benzene (with D substituent) — L — NH — benzene (with E and M substituents)]

| Compound No | A | Q | L | D | E | M | Substituted Position on Naphthalene[1] | Substituted Position on Benzene[2] |
|---|---|---|---|---|---|---|---|---|
| 1206 | benzyl-O— (PhCH$_2$O—) | 0 | CO | H | CO$_2$H | H | 2-position | para |
| 1207 | HO | 0 | CH$_2$CO | H | CO$_2$Me | H | 2-position | para |
| 1208 | HO | 0 | CH$_2$CO | H | CO$_2$H | H | 2-position | para |
| 1209 | t-BuO— | 0 | CH$_2$CO | H | CO$_2$Me | H | 2-position | para |
| 1210 | t-BuO— | 0 | CH$_2$CO | H | CO$_2$H | H | 2-position | para |
| 1211 | cyclohexyl-O— | 0 | CH$_2$CO | H | CO$_2$Me | H | 2-position | para |
| 1212 | cyclohexyl-O— | 0 | CH$_2$CO | H | CO$_2$H | H | 2-position | para |
| 1213 | n-C$_8$H$_{17}$O— | 0 | CH$_2$CO | H | CO$_2$Me | H | 2-position | para |
| 1214 | n-C$_8$H$_{17}$O— | 0 | CH$_2$CO | H | CO$_2$H | H | 2-position | para |

[1]Position substituted by Q on naphthalene ring
[2]Relative position of Q and L on the benzene ring that has been substituted by Q, L and D

TABLE 1-4

| Compound No | A | Q | L | D | E | M | Substituted Position on Naphthalene[1] | Substituted Position on Benzene[2] |
|---|---|---|---|---|---|---|---|---|
| 1215 | phenyl-O-(CH$_2$)$_3$-CH$_2$-O- | O | CH$_2$ | CO | H | CO$_2$Me | H | 2-position | para |
| 1216 | phenyl-O-(CH$_2$)$_3$-CH$_2$-O- | O | CH$_2$ | CO | H | CO$_2$H | H | 2-position | para |
| 1217 | CH$_2$=CH-CH$_2$-O- | O | CH$_2$ | CO | H | CO$_2$Me | H | 2-position | para |
| 1218 | CH$_2$=CH-CH$_2$-O- | O | CH$_2$ | CO | H | CO$_2$H | H | 2-position | para |
| 1219 | CH$_2$=CH-CH$_2$-CH$_2$-CH$_2$-O- | O | CH$_2$ | CO | H | CO$_2$Me | H | 2-position | para |
| 1220 | CH$_2$=CH-CH$_2$-CH$_2$-CH$_2$-O- | O | CH$_2$ | CO | H | CO$_2$H | H | 2-position | para |
| 1221 | geranyl-O- | O | CH$_2$ | CO | H | CO$_2$Me | H | 2-position | para |
| 1222 | geranyl-O- | O | CH$_2$ | CO | H | CO$_2$H | H | 2-position | para |
| 1223 | PhCH$_2$-O- | O | CH$_2$ | CO | H | CO$_2$Me | H | 2-position | para |
| 1224 | PhCH$_2$-O- | O | CH$_2$ | CO | H | CO$_2$H | H | 2-position | para |

[1] Position substituted by Q on naphthalene ring
[2] Relative position of Q and L on the benzene ring that has been substituted by Q, L and D

TABLE 1-5

[Structure: naphthalene with substituent A at 6-position, linked via Q-O to a benzene ring (with D substituent) which is linked via L to NH, which connects to another benzene ring (with E and M substituents)]

| Compound No. | A | Q | L | D | E | M | Substituted Position on Naphthalene[*1)] | Substituted Position on Benzene[*2)] |
|---|---|---|---|---|---|---|---|---|
| 1225 | 3-phenylpropyl-O- | 0 | $CH_2$ CO | H | $CO_2$ Me | H | 2-position | para |
| 1226 | 3-phenylpropyl-O- | 0 | $CH_2$ CO | H | $CO_2$ H | H | 2-position | para |
| 1227 | (naphthalen-2-yl)methyl-O- | 0 | $CH_2$ CO | H | $CO_2$ Me | H | 2-position | para |
| 1228 | (naphthalen-2-yl)methyl-O- | 0 | $CH_2$ CO | H | $CO_2$ H | H | 2-position | para |
| 1149 | H | 0 | CH(Me)CO | H | $CO_2$ Me | H | 2-position | para |
| 1150 | H | 0 | CH(Me)CO | H | $CO_2$ H | H | 2-position | para |
| 1151 | H | 0 | $CH(Me)_2$ CO | H | $CO_2$ Me | H | 2-position | para |
| 1152 | H | 0 | $CH(Me)_2$ CO | H | $CO_2$ H | H | 2-position | para |
| 1153 | H | 0 | CO | H | $CO_2$ Me | 3-Me | 2-position | para |
| 1154 | H | 0 | CO | H | $CO_2$ H | 3-Me | 2-position | para |
| 1155 | H | 0 | $CH_2$ CO | H | $CO_2$ Me | 4-$NO_2$ | 2-position | para |
| 1156 | H | 0 | $CH_2$ CO | H | $CO_2$ H | 4-$NO_2$ | 2-position | para |
| 1157 | H | 0 | $CH_2$ CO | H | $CO_2$ Me | 4-F | 2-position | para |
| 1158 | H | 0 | $CH_2$ CO | H | $CO_2$ H | 4-F | 2-position | para |
| 1159 | H | 0 | $CH_2$ CO | H | $CO_2$ Me | 5-F | 2-position | para |
| 1160 | H | 0 | $CH_2$ CO | H | $CO_2$ H | 5-F | 2-position | para |
| 1161 | H | 0 | $CH_2$ CO | H | $CO_2$ Me | 5-Cl | 2-position | para |
| 1162 | H | 0 | $CH_2$ CO | H | $CO_2$ H | 5-Cl | 2-position | para |
| 1163 | H | 0 | $CH_2$ CO | H | $CO_2$ Me | 6-Me | 2-position | para |
| 1164 | H | 0 | $CH_2$ CO | H | $CO_2$ H | 6-Me | 2-position | para |

[*1)] Position substituted by Q on naphthalene ring
[*2)] Relative position of Q and L on the benzene ring that has been substituted by Q, L and D

TABLE 1-6

| Compound No. | A | Q | L | D | E | M | Substituted Position on Naphthalene*[1] | Substituted Position on Benzene*[2] |
|---|---|---|---|---|---|---|---|---|
| 1229 | MeO | 0 | CH$_2$ CO | H | CO$_2$ Me | H | 2-position | para |
| 1230 | MeO | 0 | CH$_2$ CO | H | CO$_2$ H | H | 2-position | para |
| 1231 | (tert-butyl-O-) | 0 | CO | H | CO$_2$ Me | H | 2-position | para |
| 1232 | (tert-butyl-O-) | 0 | CO | H | CO$_2$ H | H | 2-position | para |
| 1233 | (cyclohexyl-O-) | 0 | CO | H | CO$_2$ Me | H | 2-position | para |
| 1234 | (cyclohexyl-O-) | 0 | CO | H | CO$_2$ H | H | 2-position | para |
| 1235 | (octyl-O-) | 0 | CO | H | CO$_2$ Me | H | 2-position | para |
| 1236 | (octyl-O-) | 0 | CO | H | CO$_2$ H | H | 2-position | para |

*[1]Position substituted by Q on naphthalene ring
*[2]Relative position of Q and L on the benzene ring that has been substituted by Q, L and D

TABLE 1-7

| Compound No. | A | Q | L | D | E | M | Substituted Position on Naphthalene*[1] | Substituted Position on Benzene*[2] |
|---|---|---|---|---|---|---|---|---|
| 1237 | (phenyl-O-(CH$_2$)$_4$-O-) | 0 | CO | H | CO$_2$ Me | H | 2-position | para |

TABLE 1-7-continued

[Structure: naphthalene with A substituent, linked via Q-O to benzene ring bearing D, then L, NH, to another benzene with E and M substituents]

| Compound No. | A | Q | L | D | E | M | Substituted Position on Naphthalene[1] | Substituted Position on Benzene[2] |
|---|---|---|---|---|---|---|---|---|
| 1238 | phenoxybutyl-O- | 0 | CO | H | $CO_2H$ | H | 2-position | para |
| 1239 | allyl-O- | 0 | CO | H | $CO_2Me$ | H | 2-position | para |
| 1240 | allyl-O- | 0 | CO | H | $CO_2H$ | H | 2-position | para |
| 1241 | butenyl-O- | 0 | CO | H | $CO_2Me$ | H | 2-position | para |
| 1242 | butenyl-O- | 0 | CO | H | $CO_2H$ | H | 2-position | para |
| 1243 | geranyl-O- | 0 | CO | H | $CO_2Me$ | H | 2-position | para |
| 1244 | geranyl-O- | 0 | CO | H | $CO_2H$ | H | 2-position | para |

[1] Position substituted by Q on naphthalene ring
[2] Relative position of Q and L on the benzene ring that has been substituted by Q, L and D

TABLE 1-8

[Structure as above]

| Compound No. | A | Q | L | D | E | M | Substituted Position on Naphthalene[1] | Substituted Position on Benzene[2] |
|---|---|---|---|---|---|---|---|---|
| 1247 | phenylpropyl-O- | 0 | CO | H | $CO_2Me$ | H | 2-Position | para |
| 1248 | phenylpropyl-O- | 0 | CO | H | $CO_2H$ | H | 2-Position | para |

TABLE 1-8-continued

[Structure: naphthalene-A with O-Q linker to benzene ring bearing D, then L-NH linker to benzene bearing E, M]

| Compound No. | A | Q | L | D | E | M | Substituted Position on Naphthalene[1] | Substituted Position on Benzene[2] |
|---|---|---|---|---|---|---|---|---|
| 1249 | 2-naphthylmethyl-O | 0 | CO | H | $CO_2$Me | H | 2-Position | para |
| 1250 | 2-naphthylmethyl-O | 0 | CO | H | $CO_2$H | H | 2-Position | para |

[1] Position substituted by Q on naphthalene ring
[2] Relative position of Q and L on the benzene ring that has been substituted by Q, L and D

TABLE 1-9

[Structure: naphthalene-A with O-Q linker to benzene ring bearing D, then L-NH linker to benzene bearing E, M]

| Compound No. | A | Q | L | D | E | M | Substituted Position on Naphthalene[1] | Substituted Position on Benzene[2] |
|---|---|---|---|---|---|---|---|---|
| 1251 | HO | 0 | CO | $NO_2$ | $CO_2$Me | H | 2-Position | para |
| 1252 | HO | 0 | CO | $NO_2$ | $CO_2$H | H | 2-Position | para |
| 1253 | MeO | 0 | CO | $NO_2$ | $CO_2$Me | H | 2-Position | para |
| 1254 | MeO | 0 | CO | $NO_2$ | $CO_2$H | H | 2-Position | para |
| 1255 | benzyl-O | 0 | CO | $NO_2$ | $CO_2$Me | H | 2-Position | para |
| 1256 | benzyl-O | 0 | CO | $NO_2$ | $CO_2$H | H | 2-Position | para |
| 1257 | HO | 0 | $CH_2$CO | $NO_2$ | $CO_2$Me | H | 2-Position | para |
| 1258 | HO | 0 | $CH_2$CO | $NO_2$ | $CO_2$H | H | 2-Position | para |
| 1259 | t-Bu-O | 0 | $CH_2$CO | $NO_2$ | $CO_2$Me | H | 2-Position | para |
| 1260 | t-Bu-O | 0 | $CH_2$CO | $NO_2$ | $CO_2$H | H | 2-Position | para |

TABLE 1-9-continued

| Compound No. | A | Q | L | D | E | M | Substituted Position on Naphthalene[*1)] | Substituted Position on Benzene[*2)] |
|---|---|---|---|---|---|---|---|---|
| 1261 | cyclohexyl-O | 0 | $CH_2$ CO | $NO_2$ | $CO_2$ Me | H | 2-Position | para |
| 1262 | cyclohexyl-O | 0 | $CH_2$ CO | $NO_2$ | $CO_2$ H | H | 2-Position | para |
| 1264 | heptyl-O | 0 | $CH_2$ CO | $NO_2$ | $CO_2$ Me | H | 2-Position | para |
| 1264 | heptyl-O | 0 | $CH_2$ CO | $NO_2$ | $CO_2$ H | H | 2-Position | para |

[*1)]Position substituted by Q on naphthalene ring
[*2)]Relative position of Q and L on the benzene ring that has been substituted by Q, L and D

TABLE 1-10

| Compound No. | A | Q | L | D | E | M | Substituted Position on Naphthalene[*1)] | Substituted Position on Benzene[*2)] |
|---|---|---|---|---|---|---|---|---|
| 1265 | PhO-(CH$_2$)$_4$-O | 0 | $CH_2$ CO | $NO_2$ | $CO_2$ Me | H | 2-Position | para |
| 1266 | PhO-(CH$_2$)$_4$-O | 0 | $CH_2$ CO | $NO_2$ | $CO_2$ H | H | 2-Position | para |
| 1267 | allyl-O | 0 | $CH_2$ CO | $NO_2$ | $CO_2$ Me | H | 2-Position | para |
| 1268 | allyl-O | 0 | $CH_2$ CO | $NO_2$ | $CO_2$ H | H | 2-Position | para |
| 1269 | pentenyl-O | 0 | $CH_2$ CO | $NO_2$ | $CO_2$ Me | H | 2-Position | para |
| 1270 | pentenyl-O | 0 | $CH_2$ CO | $NO_2$ | $CO_2$ H | H | 2-Position | para |

TABLE 1-10-continued

| Compound No. | A | Q | L | D | E | M | Substituted Position on Naphthalene[*1] | Substituted Position on Benzene[*2] |
|---|---|---|---|---|---|---|---|---|
| 1271 | (2,6-dimethyl-2,6-octadienyl)oxy | 0 | $CH_2 CO$ | $NO_2$ | $CO_2 Me$ | H | 2-Position | para |
| 1272 | (2,6-dimethyl-2,6-octadienyl)oxy | 0 | $CH_2 CO$ | $NO_2$ | $CO_2 H$ | H | 2-Position | para |
| 1273 | benzyloxy | 0 | $CH_2 CO$ | $NO_2$ | $CO_2 Me$ | H | 2-Position | para |
| 1274 | benzyloxy | 0 | $CH_2 CO$ | $NO_2$ | $CO_2 H$ | H | 2-Position | para |

[*1] Position substituted by Q on naphthalene ring
[*2] Relative position of Q and L on the benzene ring that has been substituted by Q, L and D

TABLE 1-11

| Compound No. | A | Q | L | D | E | M | Substituted Position on Naphthalene[*1] | Substituted Position on Benzene[*2] |
|---|---|---|---|---|---|---|---|---|
| 1275 | 3-phenylpropyloxy | 0 | $CH_2 CO$ | $NO_2$ | $CO_2 Me$ | H | 2-Position | para |
| 1276 | 3-phenylpropyloxy | 0 | $CH_2 CO$ | $NO_2$ | $CO_2 H$ | H | 2-Position | para |
| 1277 | (2-naphthyl)methoxy | 0 | $CH_2 CO$ | $NO_2$ | $CO_2 Me$ | H | 2-Position | para |

TABLE 1-11-continued

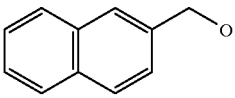

| Compound No. | A | Q | L | D | E | M | Substituted Position on Naphthalene[*1] | Substituted Position on Benzene[*2] |
|---|---|---|---|---|---|---|---|---|
| 1278 | (2-naphthylmethyleneoxy) | 0 | $CH_2$ CO | $NO_2$ | $CO_2$ H | H | 2-Position | para |

[*1] Position substituted by Q on naphthalene ring
[*2] Relative position of Q and L on the benzene ring that has been substituted by Q, L and D

TABLE 1-12

| Compound No. | A | Q | L | D | E | M | Substituted Position on Naphthalene[*1] | Substituted Position on Benzene[*2] |
|---|---|---|---|---|---|---|---|---|
| 1279 | MeO | 0 | $CH_2$ CO | $NO_2$ | $CO_2$ Me | H | 2-Position | para |
| 1280 | MeO | 0 | $CH_2$CO | $NO_2$ | $CO_2$ H | H | 2-Position | para |
| 1281 | t-BuO | 0 | CO | $NO_2$ | $CO_2$ Me | H | 2-Position | para |
| 1282 | t-BuO | 0 | CO | $NO_2$ | $CO_2$ H | H | 2-Position | para |
| 1283 | cyclohexyl-O | 0 | CO | $NO_2$ | $CO_2$ Me | H | 2-Position | para |
| 1284 | cyclohexyl-O | 0 | CO | $NO_2$ | $CO_2$ H | H | 2-Position | para |
| 1285 | $n$-octyl-O | 0 | CO | $NO_2$ | $CO_2$ Me | H | 2-Position | para |
| 1286 | $n$-octyl-O | 0 | CO | $NO_2$ | $CO_2$ H | H | 2-Position | para |

[*1] Position substituted by Q on naphthalene ring
[*2] Relative position of Q and L on the benzene ring that has been substituted by Q, L and D

TABLE 1-13

[Structure: Naphthalene(A)-Q-phenyl(D)-L-NH-phenyl(E,M)]

| Compound No. | A | Q | L | D | E | M | Substituted Position on Naphthalene*1) | Substitiuted Position on Benzene*2) |
|---|---|---|---|---|---|---|---|---|
| 1287 | PhO-(CH$_2$)$_4$-O- | 0 | CO | NO$_2$ | CO$_2$Me | H | 2-Position | para |
| 1288 | PhO-(CH$_2$)$_4$-O- | 0 | CO | NO$_2$ | CO$_2$H | H | 2-Position | para |
| 1289 | CH$_2$=CH-CH$_2$-O- | 0 | CO | NO$_2$ | CO$_2$Me | H | 2-Position | para |
| 1290 | CH$_2$=CH-CH$_2$-O- | 0 | CO | NO$_2$ | CO$_2$H | H | 2-Position | para |
| 1291 | CH$_2$=CH-(CH$_2$)$_3$-O- | 0 | CO | NO$_2$ | CO$_2$Me | H | 2-Position | para |
| 1292 | CH$_2$=CH-(CH$_2$)$_3$-O- | 0 | CO | NO$_2$ | CO$_2$H | H | 2-Position | para |
| 1293 | geranyl-O- | 0 | CO | NO$_2$ | CO$_2$Me | H | 2-Position | para |
| 1294 | geranyl-O- | 0 | CO | NO$_2$ | CO$_2$H | H | 2-Position | para |

*1)Position substituted by Q on naphthalene ring
*2)Relative position of Q and L on the benzene ring that has been substituted by Q, L and D

TABLE 1-14

[Structure: Naphthalene(A)-Q-phenyl(D)-L-NH-phenyl(E,M)]

| Compound No. | A | Q | L | D | E | M | Substituted Position on Naphthalene*1) | Substitiuted Position on Benzene*2) |
|---|---|---|---|---|---|---|---|---|
| 1297 | Ph-(CH$_2$)$_3$-O- | 0 | CO | NO$_2$ | CO$_2$Me | H | 2-position | para |

TABLE 1-14-continued

| Compound No. | A | Q | L | D | E | M | Substituted Position on Naphthalene[*1)] | Substituted Position on Benzene[*2)] |
|---|---|---|---|---|---|---|---|---|
| 1298 | phenylpropyl-O | 0 | CO | NO$_2$ | CO$_2$H | H | 2-position | para |
| 1299 | naphthylmethyl-O | 0 | CO | NO$_2$ | CO$_2$Me | H | 2-position | para |
| 1300 | naphthylmethyl-O | 0 | CO | NO$_2$ | CO$_2$H | H | 2-position | para |

[*1)]Position substituted by Q on naphthalene ring
[*2)]Relative position of Q and L on the benzene ring that has been substituted by Q, L and D

TABLE 1-15

(A = H, M = H)

| Compound No. | Q | L | D | E | Substituted Position on Naphthalene[*1)] | Substituted Position on Benzene[*2)] |
|---|---|---|---|---|---|---|
| 3101 | S | CO | H | CO$_2$Me | 2-position | para |
| 3102 | S | CO | H | CO$_2$H | 2-position | para |
| 3103 | S | CO | H | CN | 2-position | para |
| 3104 | S | CO | H | tet | 2-position | para |
| 3105 | S | CO | NO$_2$ | CO$_2$Me | 2-position | para |
| 3106 | S | CO | NO$_2$ | CO$_2$H | 2-position | para |
| 3107 | S | CH$_2$CO | H | CO$_2$Me | 2-position | para |
| 3108 | S | CH$_2$CO | H | CO$_2$H | 2-position | para |
| 3109 | S | CH$_2$CO | H | CN | 2-position | para |
| 3110 | S | CH$_2$CO | H | tet | 2-position | para |
| 3111 | S | CH$_2$CO | NO$_2$ | CO$_2$Me | 2-position | para |
| 3112 | S | CH$_2$CO | NO$_2$ | CO$_2$H | 2-position | para |
| 3113 | S | CH$_2$CH$_2$CO | H | CO$_2$Me | 2-position | para |
| 3114 | S | CH$_2$CH$_2$CO | H | CO$_2$H | 2-position | para |
| 3115 | S | CH=CHCO | H | CO$_2$Me | 2-position | para |
| 3116 | S | CH=CHCO | H | CO$_2$H | 2-position | para |

[*1)]Position substituted by Q on naphthalene ring
[*2)]Relative position of Q and L on the benzene ring that has been substituted by Q, L and D

TABLE 1-16

(A = H, M = H)

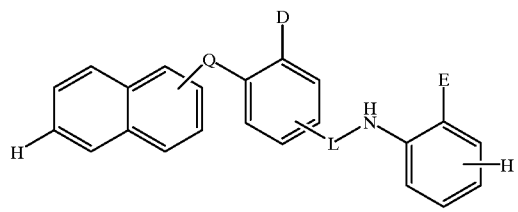

| Compound No. | Q | L | D | E | Substituted Position on Naphthalene*[1] | Substituted Position on Benzene*[2] |
|---|---|---|---|---|---|---|
| 4101 | $CH_2$ | CO | H | $CO_2$ Me | 2-position | para |
| 4102 | $CH_2$ | CO | H | $CO_2$ Et | 2-position | para |
| 4103 | $CH_2$ | CO | H | $CO_2$ H | 2-position | para |
| 4104 | $CH_2$ | CO | H | H | 2-position | para |
| 4105 | $CH_2$ | CO | H | OH | 2-position | para |
| 4106 | $CH_2$ | CO | H | $SO_2 NH_2$ | 2-position | para |
| 4107 | $CH_2$ | CO | H | tet | 2-position | para |
| 4108 | $CH_2$ | CO | H | $CO_2$ Me | 1-position | para |
| 4109 | $CH_2$ | CO | H | $CO_2$ H | 1-position | para |
| 4110 | $CH_2$ | CO | $NO_2$ | $CO_2$ Me | 2-position | para |
| 4111 | $CH_2$ | CO | $NO_2$ | $CO_2$ H | 2-position | para |
| 4112 | $CH_2$ | $CH_2$ CO | H | $CO_2$ Me | 2-position | para |
| 4113 | $CH_2$ | $CH_2$ CO | H | $CO_2$ Et | 2-position | para |
| 4114 | $CH_2$ | $CH_2$ CO | H | $CO_2$ H | 2-position | para |
| 4115 | $CH_2$ | $CH_2$ CO | H | H | 2-position | para |
| 4116 | $CH_2$ | $CH_2$ CO | H | OH | 2-position | para |
| 4117 | $CH_2$ | $CH_2$ CO | H | $SO_2 NH_2$ | 2-position | para |
| 4118 | $CH_2$ | $CH_2$ CO | H | tet | 2-position | para |
| 4119 | $CH_2$ | $CH_2$ CO | H | $CO_2$ Me | 1-position | para |
| 4120 | $CH_2$ | $CH_2$ CO | H | $CO_2$ H | 1-position | para |
| 4121 | $CH_2$ | $CH_2$ CO | $NO_2$ | $CO_2$ Me | 2-position | para |
| 4122 | $CH_2$ | $CH_2$ CO | $NO_2$ | $CO_2$ H | 2-position | para |
| 4123 | $CH_2$ | $CH_2$ $CH_2$ CO | H | $CO_2$ Me | 2-positlon | para |
| 4124 | $CH_2$ | $CH_2$ $CH_2$ CO | H | $CO_2$ H | 2-position | para |
| 4125 | $CH_2$ | CH=CHCO | H | $CO_2$ Me | 2-position | para |
| 4126 | $CH_2$ | CH=CHCO | H | $CO_2$ H | 2-position | para |

*[1] Position substituted by Q on naphthalene ring
*[2] Relative position of Q and L on the benzene ring that has been substituted by Q, L and D

TABLE 1-17

(A = H, M = H)

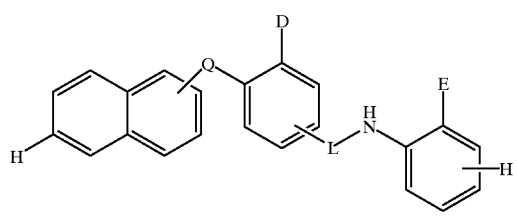

| Compound No. | Q | L | D | E | Substituted Position on Naphthalene*[1] | Substituted Position on Benzene*[2] |
|---|---|---|---|---|---|---|
| 5101 | $OCH_2$ | CO | H | $CO_2$ Me | 2-position | para |
| 5102 | $OCH_2$ | CO | H | $CO_2$ H | 2-position | para |
| 5103 | $OCH_2$ | $CH_2$ CO | H | $CO_2$ Me | 2-position | para |
| 5104 | $OCH_2$ | $CH_2$ CO | H | $CO_2$ H | 2-position | para |
| 6101 | $SCH_2$ | CO | H | $CO_2$ Me | 2-position | para |
| 6102 | $SCH_2$ | CO | H | $CO_2$ H | 2-position | para |
| 6103 | $SCH_2$ | $CH_2$ CO | H | $CO_2$ Me | 2-position | para |
| 6104 | $SCH_2$ | $CH_2$ CO | H | $CO_2$ H | 2-position | para |
| 7101 | CO | CO | H | $CO_2$ Me | 2-position | para |
| 7102 | CO | CO | H | $CO_2$ H | 2-position | para |
| 7103 | CO | CO | H | $CO_2$ Me | 1-position | para |

TABLE 1-17-continued (A = H, M = H)

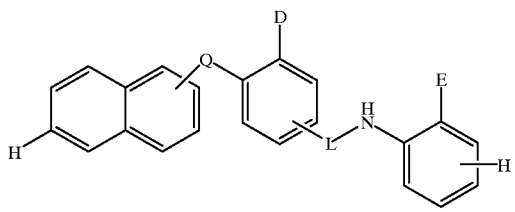

| Compound No. | Q | L | D | E | Substituted Position on Naphthalene[*1)] | Substituted Position on Benzene[*2)] |
|---|---|---|---|---|---|---|
| 7104 | CO | CO | H | $CO_2H$ | 1-position | para |
| 7105 | CO | $CH_2$ CO | H | $CO_2$ Me | 2-position | para |
| 7106 | CO | $CH_2$ CO | H | $CO_2H$ | 2-position | para |
| 8101 | CH(OMe) | CO | H | $CO_2$ Me | 2-position | para |
| 8102 | CH(OMe) | CO | H | $CO_2H$ | 2-position | para |
| 8103 | CH(OMe) | CO | $NO_2$ | $CO_2$ Me | 2-position | para |
| 8104 | CH(OMe) | CO | $NO_2$ | $CO_2H$ | 2-position | para |
| 8105 | CH(OMe) | $CH_2$ CO | H | $CO_2$ Me | 2-position | para |
| 8106 | CH(OMe) | $CH_2$ CO | H | $CO_2H$ | 2-position | para |
| 8107 | CH(OMe) | $CH_2$ CO | $NO_2$ | $CO_2$ Me | 2-position | para |
| 8108 | CH(OMe) | $CH_2$ CO | $NO_2$ | $CO_2H$ | 2-position | para |

[*1)]Position substituted by Q naphthalene ring
[*2)]Relative position of Q and L on the benzene ring that has been substituted by Q, L and D

TABLE 1-18

(A = H, M = H)

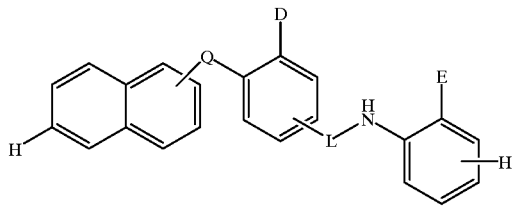

| Compound No. | Q | L | D | E | Substituted Position on Naphthalene[*1)] | Substituted Position on Benzene[*2)] |
|---|---|---|---|---|---|---|
| 8109 | CH(OEt) | CO | H | $CO_2$ Me | 2-position | para |
| 8110 | CH(OEt) | CO | H | $CO_2H$ | 2-position | para |
| 8111 | CH(OEt) | CO | $NO_2$ | $CO_2$ Me | 2-position | para |
| 8112 | CH(OEt) | CO | $NO_2$ | $CO_2H$ | 2-position | para |
| 8113 | CH(OEt) | $CH_2$ CO | H | $CO_2$ Me | 2-position | para |
| 8114 | CH(OEt) | $CH_2$ CO | H | $CO_2H$ | 2-position | para |
| 8115 | CH(OEt) | $CH_2$ CO | $NO_2$ | $CO_2$ Me | 2-position | para |
| 8116 | CH(OEt) | $CH_2$ CO | $NO_2$ | $CO_2H$ | 2-position | para |

[*1)]Position substituted by Q on naphthalene ring
[*2)]Relative position of Q and L on the benzene ring that has been substituted by Q, L and D The naphthalene derivatives of this invention represented by formula [I], their pharmacologically acceptable salts, or their pharmacologically acceptable solvates can be prepared, for example, by the following scheme except the compounds in which A is a hydroxy group or D is an amino group. Namely, a carboxylic acid [III] having a naphthalene moiety is condensed with an aniline derivative [IV], to afford target compound [I].

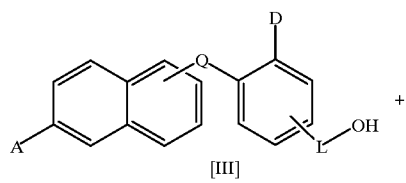

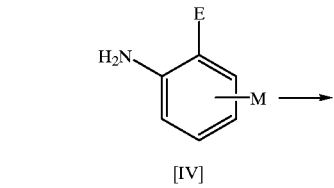

[IV]

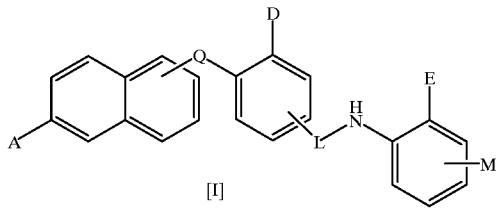

[I]

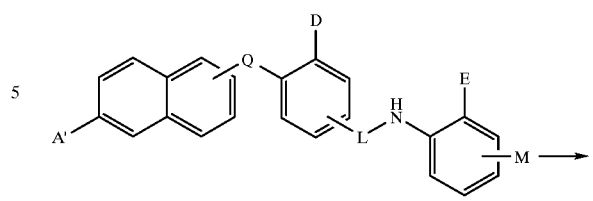

[VII]

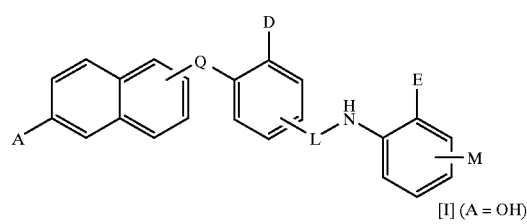

[I] (A = OH)

What A, Q, L, D, E and M stands for in above formulas is as defined above.

The starting material [III] can be obtained by a method publicly known.

The condensation can be performed by two methods: one with the use of an acyl halide, and the other without the use of an acyl halide. These two methods are basically known.

For the compound [I] prepared by way of an acyl halide, the compound [III] is allowed to react with a halogenating agent such as oxalyl chloride or thionyl chloride under the presence or absence of an additive such as DMF or the like, to give an acyl halide of [III] which is then allowed to react with the compound [IV] under the presence or absence of a base, to give the compound [I].

On the other hand, with the method in which an acyl halide is not utilized, the compound [III] is activated by the use of one of various activators such as anhydrous mixed acids, carbodiimides, imidazoles, haloester phosphates, cyanoester phosphates, etc., and the resulting compound is allowed to react with the compound [IV] to give the compound [I].

Further, when the naphthalene derivative of this invention represented by formula [I], its pharmacologically acceptable salt, or its pharmacologically acceptable solvate has a hydroxy group as A, it can be prepared, for example, by the following scheme. Namely, a carboxylic acid [V] having a naphthalene moiety which has been substituted by A' whose hydroxy group has been protected by an appropriate protecting group is condensed with an aniline derivative [VI] to produce a compound [VII]. The compound [VII] is then deprotected to give the compound [I](A=OH).

The definitions of A, Q, L, D, E and M in above formulas are as described above. A' represents a hydrogen group protected by an appropriate protecting group.

The protecting group and its removal method may occur in following combinations to take representative examples: A' having its hydroxy group protected by a methoxy group and deprotected by Me₃SiI, EtSNa or BBr₃; A' having its hydroxy group protected by an allyloxy group and deprotected by Paradium catalyst; and A' having its hydroxy group protected by a benzyloxy group and deprotected by hydrogenation.

The starting material [V] can be obtained by a publicly known method.

The condensation of the compounds [V] and [VI] can be performed in the same manner as in the condensation of the compounds [III] and [IV] described above.

Further, when the naphthalene derivative of this invention represented by formula [I], its pharmacologically acceptable salt, or its pharmacologically acceptable solvate has an amino group as D, it can be prepared, for example, by the following scheme. Namely, carboxylic acid [VIII], having a naphthalene moiety and a protected amino substituent or a substituent convertible into amino group as D', is condensed with aniline derivative [IX] to give compound [X]. Compound [X] is deprotected or converted to an amino group, to give the compound [I] (D=NH₂).

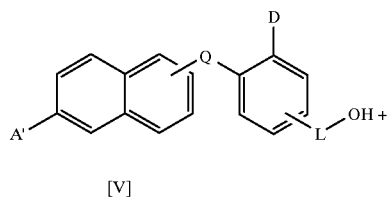

[V]

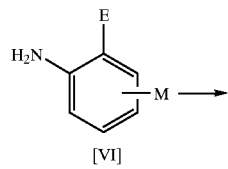

[VI]

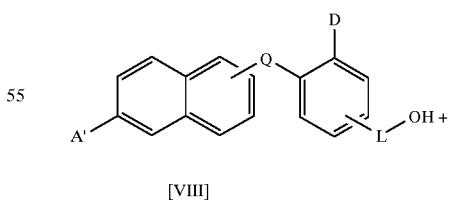

[VIII]

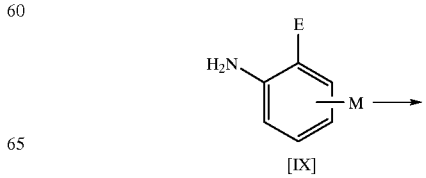

[IX]

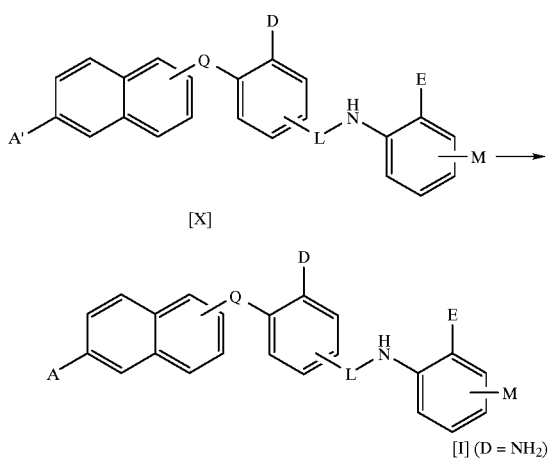

[X]

[I] (D = NH₂)

The definitions of A, Q, L, D, E and M in above formulas are as described above. D' represents an amino group protected by an appropriate protecting group, or a functional group convertible to an amino group.

Representative examples of the protecting group and its removal method are listed in following combinations: D' having its amino group protected by a benzyl carbamoyl group and deprotected by hydrogenation; D' having its amino group protected by 9-fluorenylmethyl carbamoyl group and deprotected by an organic base such as piperidine; and D' having its amino group protected by t-butyl carbamoyl group and deprotected by an acid or the like. Further, the functional group convertible to an amino group includes, for example, D'=nitro group. A nitro group can be converted through a reduction reaction to an amino group.

The starting material [VIII] can be obtained by a publicly known method.

The condensation of the compounds [VIII] and [IX] can be performed as in the compounds [III] and [IV] described above.

If need be, the compound [I] thus obtained, when D represents $CO_2R^4$ wherein $R^4$ is a $C_1$–$C_4$ lower alkyl group; when E represents $CO_2R^5$ wherein $R^5$ is a $C_1$–$C_4$ lower alkyl group; or when G represents $CO_2R^6$ wherein $R^6$ is a $C_1$–$C_4$ lower alkyl group, can be hydrolyzed under an acidic or alkaline condition, to afford a compound wherein $R^4$, $R^5$ or $R^6$ represents a hydrogen atom.

Further, the compound [I] thus obtained, when E represents CN or G represents CN, is allowed to react with an azide compound to give a compound wherein E or G represents tetrazol-5-yl if it is necessary. In addition, the compound [I] thus obtained can be converted to a pharmacologically acceptable solvate as described above if it is necessary.

Furthermore, the compound [I] thus obtained (wherein D represents $CO_2R^4$ wherein $R^4$ is a hydrogen atom; E represents $CO_2R^5$ wherein $R^5$ is a hydrogen atom; G represents $CO_2R^6$ wherein $R^6$ is a hydrogen atom; E represents a tetrazol-5-yl group; G represents a tetrazol-5-yl group; or D represents $NH_2$) can be converted to a pharmacologically acceptable salt or its solvate as described above if need be.

According to above procedures, the naphthalene derivatives of this invention represented by above formula [I], their pharmacologically acceptable salts, and their pharmacologically acceptable solvates can be obtained.

The naphthalene derivatives of this invention, their pharmacologically acceptable salts or their pharmacologically acceptable solvates can be administered orally or via parenteral routes such as venous, subcutaneous, muscular, percutaneous, rectal, intranasal, ophthalmic routes, or through inhalation.

The pharmaceutical dosage formulation appropriate for oral administration includes, for example, tablets, pills, granules, powders, liquids, suspensions, syrups, capsules, etc.

Tablets can be formulated by conventional methods with an excipient(s) such as lactose, starch, crystalline cellulose or the like, a binder(s) such as carboxymethyl cellulose, methyl cellulose, polyvinyl pyrrolidone or the like, and a disintegrator(s) such as sodium alginate, sodium hydrogencarbonate, sodium laurylsulfate or the like.

Pills, granules and powders can be formulated by conventional methods with such excipient(s) and others as described above.

Liquids, suspensions and syrups can be formulated by conventional methods with glycerin esters such as tricaprylin, triacetin or the like; alcohols such as ethanol or the like; water; or vegetable oils such as corn oil, cotton seed oil, coconut oil, almond oil, peanut oil, olive oil or the like.

The compound in the form of granules, powder or liquid may be introduced into the capsules made of, say, gelatin.

For venous, subcutaneous or intramuscular injection, a sterile aqueous or nonaqueous solutions can be prepared. In order to prepare aqueous solutions from the compound, for example, physiological saline is used. In order to prepare nonaqueous solutions from the compound, used are propylene glycol, polyethylene glycol, a vegetable oil such as olive oil, or an injectable organic ester such as ethyl oleate or the like. To the preparation thus produced should be added a tonicity balancer(s), a disinfectant(s), a penetrant(s), an emulsifier(s), a dispersant(s), a stabilizer(s) and the like. The preparation can be sterilized by filtration through a filter impermeable to bacteria, by treatment with a disinfectant, or by heat or irradiation in a proper manner. In addition, a sterilized solid preparation may be produced, and just prior to use it can be dissolved in sterilized water or sterilized injection solution.

The dosage form appropriate for percutaneous application includes, for example, ointment and cream. According to the conventional methods, ointment can be formulated with oils such as castor oil, olive oil or the like, or vaseline. Cream can be formulated with fats; diethylene glycol; and an emulsifier such as sorbitan monofatty-acid ester.

The dosage form appropriate for rectal application includes typically suppositories based on the use of gelatin soft capsules.

The preparation appropriate for intranasal application includes liquid or powdery composition. The base of a liquid preparation includes water, salt water, phosphate buffer or acetate buffer. In addition, the preparation can contain a surfactant(s), an antioxidant(s), a stabilizer(s), a preserver(s), and a viscosity adjuster(s). The appropriate base for the powdery preparation should have a water-absorbing property, and includes, for example, water soluble polyacrylates such as sodium polyacrylate, potassium polyacrylate, ammonium polyacrylate or the like; cellulose lower alkylethers such as methyl cellulose, hydroxyethyl cellulose, hydroxypropyl cellulose, carboxylmethyl cellulose sodium or the like; polyethyleneglycol polyvinylpyrrolidone; amylose; and pluran; and further, water insoluble celluloses such as crystalline cellulose,-cellulose, cross-linked carboxylmethyl cellulose sodium or the like; starches such as hydroxypropyl starch, carboxymethyl starch, cross-linked starch, amylose, amylopectin, pectin or the like; proteins such as gelatin, casein, casein sodium or the like; gums such as arabic gum, tragacanth gum, glucomannan or the like; and cross-linked vinyl polymers such as polyvinyl polypyrrolidone, cross-linked polyacrylate and its salts, cross-linked polyvinyl alcohol, polyhydroxyethyl methacrylate or the like, and they can be used in combinations. To the powdery preparation can be added an antioxidant (s), a pigment(s), a preservative(s), a disinfectant(s), an antiseptic (s) or the like. The liquid or powdery preparation can be administered through a sprayer.

The dosage form appropriate for ophthalmic drop lotion is aqueous or nonaqueous solutions of the compound. For the compound to be converted to an aqueous solutions for ophthalmic use, the solvent to be used includes sterilized, purified water, physiological saline, or appropriate aqueous solvents. Thus, when it is dissolved in sterilized, purified water, it gives an aqueous solutions for ophthalmic use; when a viscosity adjuster such as carboxymethyl cellulose, methylcellulose, hydroxypropyl cellulose, polyvinyl pyrrolidone or the like is added, it gives a viscous solution for ophthalmic use; when a suspending agent such as a surfactant or a viscosity adjusting polymer is added, it gives an aqueous suspension for ophthalmic use; and when a solubilizer such as a non-ionic surfactant is added, it gives a solubilized solution for ophthalmic use. The solvent to be used for preparation of nonaqueous solutions of the compound for ophthalmic use includes nonaqueous solvents for injection. When a vegetable oil, liquid paraffin, mineral oil, propylene glycol or the like is used, the resulting fluid gives a nonaqueous solutions for ophthalmic use; when a thixotropic glue such as aluminum monostearate or the like is added, the resulting fluid gives a nonaqueous suspension for ophthalmic use. To the preparation thus produced can be added as appropriate a tonicity balancer(s), a preservative(s), a buffer(s), an emulsifier(s), a stabilizer(s) and the like. The preparation can be sterilized by filteration through a filter impermeable to bacteria, by treatment with a disinfectant, or by heat or irradiation in a proper manner. Further, a sterilized solid preparation may be produced, and just prior to use it can be dissolved or suspended in a sterilized solution.

The dosage form appropriate for ophthalmic use except eye-drop lotion includes the following. Formulation with vaseline may give an ointment for ophthalmic use; formulation with a solution such as diluted iodine tincture, zinc sulfate, methylrosalinine chloride or the like, may give a plaster for topical, ophthalmic use; minute particles, as a dispersant for ophthalmic use is applied directly; when combined with or immersed in an appropriate base or excipient, it gives a soft, long-lasting prescription to be inserted into the space behind the eye-lid.

For the inhalation, the solution or suspension of the compound in a conventional solvent(s) or excipient(s), is used as an aerosol spray. Dry powder placed lungs of the patient.

The dosage of the compound of this invention depends on the kind of the disease, the route of application, the state of the patient, and his/her age, gender and weight. The dosage appropriate for oral use in adults should be around 1–500 mg/day/head, or preferably 10–300 mg/day/head, and the dosage for parenteral application through intravenous, subcutaneous, intramuscular, percutaneous, rectal, intranasal or ophthalmic route, or through airways by inhalation should be around 0.1–100 mg/day/head, or preferably 0.3–30 mg/day/head. The compound should be so prepared as to meet above dosages. When the compound is used as a prophylactic medicine, it can be prepared according to a publicly known method, for example, in such a manner that it can give, when properly administered, a dose sufficiently preventive against a given disease to which it is indicated.

Examples described later demonstrates that the compounds inhibit IgE production in human lymphocytes exposed to antigen non-specific stimuli (IL-4+IL-10 (interleukin 10)+anti CD40Ab (anti CD40 antibody)), at a concentration showing no cytotoxicity. Accordingly, the compound of this invention is beneficial when used as a prophylactic and/or therapeutic drug for allergic diseases such as bronchial asthma, allergic rhinitis, allergic conjunctivitis, atopic dermatitis, anaphylactic shock, mite allergy, pollinosis, food allergy, urticaria, ulcerative colitis, eosinophilic gastroenteritis or the like.

Of all the compounds belonging to this invention, those that have more selective inhibitory actions against IgE than against IgG may be more useful as a prophylactic and/or therapeutic drug against allergic diseases because they can more effectively inhibit the untoward immunological reactions involved in the allergic diseases. The "selective action" here means that the compound mitigates or prevents the untoward symptons resulting from IgE production, whereas it does not affect nor scarcely affect the essential immuno responce resulted from IgG production.

Examples described later demonstrates that the compounds inhibit the production or release of chemical mediators, such as histamine and/or $LTB_4$ (leukotrien $B_4$) as well as IgE. Accordingly, the compound of this invention is beneficial when $B_4$) as well as IgE. Accordingly, the compound of this invention is beneficial when used as a prophylactic and/or therapeutic drug against the allergic diseases described above that would result from the release or production of those chemical mediators, as well as from the enhanced production of IgE antibodies.

Futher, examples specified later demonstrated that the compounds interfere with the production of TF in monocytes in human peripheral blood stream induced by lipopolysaccarides (LPS). Accordingly, the compound of this invention is beneficial when used as a prophylactic and/or therapeutic drug against the diseases that would result from the augmented production or activity of TF such as DIC; various thromboses in association with infections, autoimmune diseases including delayed immune response and SLE, various rejection reactions from transplanted organs, glomerular nephritis, viral hepatitis or the like; obstructive arteriosclerosis; cerebral embolism; cerebral infarction; pulmonary embolism; pulmonary infarction; angina pectoris; myocardial infarction; restenosis; Buerger disease; diseases involved in hypertrophic endometritis; and turbidity of an artificial crystalline lens embedded for the treatment of cataract.

The present invention will be detailed below with reference to examples. But the scope of this invention should not be limited only to those examples. The numbers attached at the end of the generic names of the compounds have the same meaning as those in Tables 1-1 to 1-18.

Example 1

Production of 2-(4-(2-naphthyloxy)benzamide) benzoic Acid Methyl Ester (Compound No. 1101)

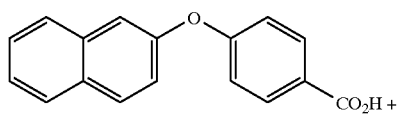

-continued

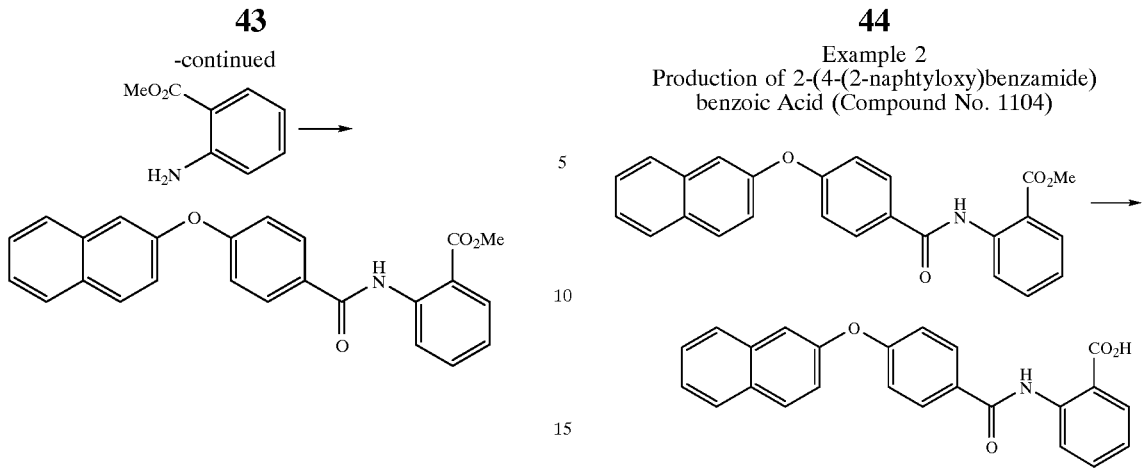

Example 2
Production of 2-(4-(2-naphtyloxy)benzamide) benzoic Acid (Compound No. 1104)

Under an atmosphere of nitrogen, 29.1 g (0.11 mol) of 4-(2-naphtyloxy)benzoate was suspended in 500 ml of dried methylene chloride, to which were added 15.4 g (0.121 mol) of oxyalyl chloride and then 10 drops of DMF with a pipette. The mixture was stirred at 35 for 2 hours. The reaction product was concentrated with an evaporator, and the residue was dissolved in 300 ml of dry methylene chloride. Under an atmosphere of nitrogen, the solution, while being cooled with ice, was added dropwise to a solution of 16.6 g (0.11 mol) of methyl anthranilate and of 12.3 g (0.121 mol) of triethyl amine in dried methylene chloride (250 ml), and the resultant mixture was stirred for 4 hours in an ice bath, and then stirred overnight at room temperature. Water was added to the reaction mixture, and extracted with methylene chloride twice. The organic phase was washed with a saturated brine, dried with anhydrous sodium sulfate, and the solvent was removed by evaporation. The residue was recrystallized from isopropyl alcohol (1.6 l) to give 40.26 g (92% yield) of 2-(4-(2-naphthyloxy)benzamide)benzoic acid methyl ester. White needle-like crystals.

$^1$H-NMR (CDCl$_3$) (ppm): 3.96(s, 3H), 7.09–7.17(m, 3H), 7.27–7.31(m, 1H), 7.42–7.53(m, 3H), 7.58–7.64(m, 1H), 7.76(d, J=8.5Hz, 1H), 7.84–7.90(m, 2H), 8.03–8.10(m, 3H), 8.93(d, J=8.3Hz, 1H), 12.02(br. s, 1H).

A 40.26 g (0.101 mol) of 2-(4-(2-naphtyloxy)benzamide) benzoic acid methyl ester obtained in Example 1 was dissolved in a mixed solvent of methanol/THF (200 ml/400 ml), to the resulting solution was added 127 ml (0.51 mol) of 4 N lithium hydroxide, and the mixture was stirred overnight at room temperature. To the reaction product was added 5 N hydrochloric acid to give a pH of about 1, and then the mixture was stirred at room temperature for 0.5 hour. Water was added to the resulting solution, and extracted with ethyl acetate twice. The organic phase was washed with brine dried with anhydrous sodium sulfate, and the solvent was removed by evaporation. The residue was recrystallized from isopropyl alcohol (1.3 l) to give 31.23 g (80% yield) of 2-(4-(2-naphthyloxy)benzamide)benzoic acid. White needle-like crystals.

$^1$H-NMR (CDCl$_3$) (ppm): 7.12–7.18(m, 3H), 7.27–7.30 (m, 1H), 7.43–7.53(m, 3H), 7.65(dt, J=1.7 and 8.6Hz, 1H), 7.76(d, J=7.6Hz, 1H), 7.85–7.91(m, 2H), 8.03(dd, J=2.0 and 6.9Hz, 2H), 8.14(dd, J=1.7 and 7.9Hz, 1H), 8.96(d, J=7.6Hz, 1H), 11.84(br. s, 1H).

Examples 3–73

In the following examples, the compounds of this invention were prepared from appropriate starting materisl according to the methods described in Examples 1 and 2. Tables 2-1 to 2-13 give the $^1$H-NMR spectrum data of the compounds thus obtained, and their yields. The compound No. in the tables represent the same with those in Tables 1-1 to 1-18. The spectrum data at the end of which (*) is attached are derived from the compounds which are dissolved in DMSO-d$_6$.

TABLE 2-1

| Example No. | Compound No. | $^1$H—NMR Spectrum Data(CDCl$_3$) δ (ppm) | Yield (%) |
|---|---|---|---|
| 3 | 1110 | 3.94(s, H), 7.11(t, J=11.1Hz, 4H), 7.4–7.7(m, 5 H), 7.72(d, J=8.2 Hz, 1H), 7.90(d, J=8.2 Hz, 1H), 8.01(s, 1H), 8.03–8.10(m, 2H), 8.90(d, J=8.5 Hz, 1H), 12.0(s, 1H). | 60 |
| 4 | 1111 | 7.00(t, J=7.2Hz, 1H), 7.11(d, J=8.9Hz, 2H), 7.18(d, J=8.0Hz, 1H), 7.34(t, J=8.3Hz, 1H), 7.50–7.61(m, 3H),7.82(d, J=8.2Hz, 1H), 7.90–8.10(m, 5H), 8.64(d, J=8.3Hz, 1H), 12.2(br.s, 1H). (*) | 62 |
| 5 | 1112 | 3.85(s, 3H), 7.11(t, J=8.3Hz, 1H), 7.20–7.30(m, 3H), 7.40–7.65(m, 5H), 7.70–7.90(m, 4H), 8.05(d, J=7.3Hz, 1H), 8.88(d, J=9.2Hz, 1H), 12.0(s, 1H), | 66 |
| 6 | 1113 | 7.01(t, J=7.4Hz, 1H), 7.20–7.40(m, 3H), 7.40–7.55(m, 3H), 7.58(t, J=7.9Hz, 1H), 7.69(s, 1H), 7.85(d, J=7.6Hz, 1H), 7.92(d, J=1.7Hz, 1H), 7.95(s, 1H), 8.00(d, J=8.9Hz, 1H), 8.05(d, J=8.6Hz, 1H), 8.62(d, J=7.9Hz, 1H), 12.1(br.s, 1H). (*) | 65 |
| 7 | 1114 | 3.95(s, 3H), 7.05–7.20(m, 2H), 7.25–7.35(m, 2H), 7.45–7.60(m, 3H), 7.70–7.90(m, 2H), 7.93(d, J=1.3Hz, 1H), 8.11(dt, J=1.3 and 10.0Hz, 1H), 8.70(d, J=2.3Hz, 1H), 8.87(d, J=7.6Hz, 1H), 12.2(s, 1H). | 98 |

TABLE 2-1-continued

| Example No. | Compound No. | $^1$H—NMR Spectrum Data(CDCl$_3$) δ (ppm) | Yield (%) |
|---|---|---|---|
| 8 | 1116 | 7.24(t, J=7.2Hz, 1H), 7.34(d, J=8.5Hz, 1H), 7.43(dd, J=2.6 and 4.5Hz, 1H), 7.50–7.60(m, 2H), 7.60–7.70(m, 2H), 7.95(dd, J=8.1 and 14.6Hz, 2H), 8.06(dd, J=7.6 and 8.0Hz, 2H), 8.20–8.25(m, 2H), 8.60–8.70(m, 2H), 12.3(s, 1H). (*) | 34 |
| 9 | 1120 | 6.95(d, J=8.6Hz, 1H), 7.16(t, J=7.6Hz, 1H), 7.43–7.62(m, 4H), 7.73(d, J=2.3Hz, 1H), 7.88–8.07(m, 4H), 8.55(s, 1H), 8.70(d,J=7.9Hz, 1H), (*) | 55 |

TABLE 2-2

| Example No. | Compound No. | $^1$H—NMR Spectrum Data(CDCl$_3$) | Yield (%) |
|---|---|---|---|
| 10 | 1121 | 3.82(s, 3H), 3.98(s, 3H), 6.99–7.03(m, 1H), 7.11–7.15(m, 2H), 7.40–7.65(m, 6H), 7.78–8.10(m, 6H), 8.84–8.96(m, 3H), 12.10(br.s, 1H), 12.24(br.s, 1H). | 14 |
| 11 | 1122 | 7.10(d, J=8.6Hz, 1H), 7.21(t, J=7.9Hz, 1H), 7.47–7.55(m, 3H), 7.66–7.69(m, 2H), 7.75(s, 1H), 7.90–8.12(m, 6H), 8.70–8.78(m, 3H), 12.42(br.s, 2H). (*) | 87 |
| 12 | 1123 | 3.77(s, 2H), 3.89(s, 3H), 7.05–7.11(m, 3H), 7.27–7.57(m, 7H), 7.69(d, J=7.6Hz, 1H), 7.82(d, J=8.6Hz, 2H), 8.01(dd, J=1.7 and 7.9 Hz, 1H), 8.73(d, J=8.6Hz, 1H), 11.10(br.s, 1H). | 65 |
| 13 | 1126 | 3.80(s, 2H), 7.04(t, J=7.6Hz, 1H), 7.09–7.14(m, 2H), 7.21–7.29(m, 2H), 7.34–7.45(m, 4H), 7.54–7.65(m, 2H), 7.76(d, J=8.6Hz, 2H), 8.07(dd, J=1.7 and 7.9Hz, 2H), 8.76(dd, J=1.0 and 8.6Hz, 1H), 10.74(br.s, 1H), | 81 |
| 14 | 1145 | 2.78(t, J=7.3Hz, 2H), 3.09(t, J=7.3Hz, 2H), 3.92(s, 3H), 6.99–7.03(m, 2H), 7.05–7.12(m, 1H), 7.22–7.27(m, 4H), 7.41(dquint, J=1.3 and 6.9Hz, 2H), 7.55(dt, J=1.7 and 6.9Hz, 1H), 7.67(d, J=7.6Hz, 1H), 7.81(d, J=8.6Hz, 2H), 8.03(dd, J=1.7 and 7.9Hz, 1H), 8.73(dd, J=1.0 and 8.6Hz, 1H), 11.09(br.s, 1H), | 90 |
| 15 | 1146 | 2.78(t, J=7.9Hz, 2H). 3.09(t, J=7.9Hz, 2H), 6.97–7.02(m, 2H), 7.12(dt, J=1.0 and 7.3Hz, 1H), 7.20–7.27(m, 4H), 7.41(dquint, J=1.3 and 6.9Hz, 2H), 7.57–7.68(m, 2H), 7.80(d, J=8.9Hz, 2H), 8.10(dd, J=1.7 and 7.9Hz, 1H), 8.76(dd, J=1.0 and 8.6Hz, 1H), 10.87(br.s, 1H). | 69 |

TABLE 2-3

| Example No. | Compound No. | $^1$H—NMR Spectrum Data(CDCl$_3$) δ (ppm) | Yield (%) |
|---|---|---|---|
| 16 | 1147 (trans-) | 3.96(s, 3H), 6.55(d, J=15.5Hz, 1H), 7.04–7.13(m, 3H), 7.25–7.31(m, 1H), 7.41–7.52(m, 3H), 7.56–7.62(m, 3H), 7.72–7.78(m, 2H), 7.83–7.89(m, 2H), 8.06(dd, J=1.7 and 7.9Hz, 1H), 8.88(dd, J=1.0 and 8.6Hz, 1H), 11.35(br.s, 1H). | 85 |
| 17 | 1148 (trans-) | 6.54(d, J=15.5Hz, 1H), 7.05–7.08(m, 2H), 7.11–7.17(m, 1H), 7.24–7.29(m, 1H), 7.40–7.52(m, 3H), 7.56–7.65(m, 3H) 7.67–7.88(m, 4H), 8.15(dd, J=1.7 and 8.2Hz, 1H) 8.91(dd, J=1.0 and 8.6Hz, 1H), 11.16(br.s, 1H). | 84 |
| 18 | 3101 | 3.94(s, 3H), 7.11(t, J=7.3Hz, 1H). 7.35(d, J=8.3Hz, 2H), 7.49–7.63(m, 4H), 7.79–7.89(m, 3H), 7.94(d, J=8.6Hz, 2H), 8.04(d, J=1.3Hz, 1H), 8.07(dd, J=1.7 and 8.3Hz, 1H), 8.91(d, J=7.9Hz, 1H), 12.02(br.s, 1H), | 83 |
| 19 | 3102 | 7.15(t, J=7.6Hz, 1H), 7.34(d, J=8.6Hz, 2H), 7.49–7.65(m, 4H), 7.80–7.92(m, 5H), 8.04(s, 1H), 8.13(dd, J=2.0 and 8.3Hz, 1H), 8.93 (d, J=8.3Hz, 1H), 11.84(br.s, 1H). | 91 |

TABLE 2-4

| Example No. | Compound No. | $^1$H—NMR Spectrum Data(CDCl$_3$) δ (ppm) | Yield (%) |
|---|---|---|---|
| 20 | 1203 | 3.93(s, 3H), 3.95(s, 3H), 7.09–7.24(m, 6H), 7.42(d, J=2Hz, 1H), 7.61(t, J=7Hz, 1H), 7.67(d, J=10Hz, 1H), 7.78(d, J=9Hz, 1H), 8.04(d, J=9Hz, 2H), 8.08(dd, J=2 and 8Hz, 1H), 8.93(d, J=9Hz, 1H), 12.01(br.s, 1H). | 45 |

TABLE 2-4-continued

| Example No. | Compound No. | ¹H—NMR Spectrum Data(CDCl₃) δ (ppm) | Yield (%) |
|---|---|---|---|
| 21 | 1204 | 3.98(s, 3H), 7.08–7.26(m, 6H), 7.42(d, J=2Hz, 1H), 7.65–7.73(m, 3H), 8.00–8.26(m, 3H), 8.96(d, J=9Hz, 1H), 11.87 (br.s, 1H), | 67 |
| 22 | 1205 | 3.95(s, 3H), 5.20(s.2H), 7.00–7.15(m, 2H), 7.20–7.30(m, 4H), 7.35–7.45(m, 4H), 7.49(d, J=1.0Hz, 2H), 7.50–7.80(m, 1H), 7.60–7.70(m, 1H), 7.76(d, J=8.9Hz, 1H), 8.04(dd, J=2.0 and 9.9Hz, 2H), 8.10(d, J=1.7Hz, 1H), 8.90(dd, J=1.0 and 9.5 Hz, 1H), 12.0(br.s, 1H), | 56 |
| 23 | 1206 | 5.23(s, 2H), 7.17(d, J=8.7Hz, 2H), 7.20–7.45(m, 6H), 7.45–7.60(m, 4H), 7.65(t, J=7.5Hz, 1H), 7.82(d, J=8.9Hz, 1H), 7.90(d, J=8.9Hz, 1H), 7.98(d, J=8.9Hz, 2H), 8.05 (dd, J=1.7 and 8.9Hz, 1H), 8.72(d, J=8.5Hz, 1H), 12.2(br. s, 1H), 13.7(br.s, 1H). (*) | 82 |
| 24 | 1209 | 1.40(s, 9H), 3.76(s.2H), 3.88(s, 3H), 7.06(d, J=8.6Hz, 3H), 7.09–7.23(m, 2H), 7.32–7.38(m, 4H), 7.53(t, J=7.3Hz, 1H), 7.60(d, J=8.9Hz, 1H), 7.72(d, J=8.9Hz, 1H), 8.01(dd, J=1.7 and 7.9Hz, 1H), 8.73(dd, J=1.0 and 8.6Hz, 1H), 11.08(br.s, 1H). | 64 |
| 25 | 1210 | 1.40(s, 9H), 3.79(s, 2H), 7.03–7.23(m, 4H), 7.26–7.27(m, 1H), 7.33–7.36(m, 4H), 7.56(t, J=8.9Hz, 2H), 7.69(d, J=8.9Hz, 1H), 8.08(d, J=8.3Hz, 1H), 8.76(d, J=8.2Hz, 1H), 10.79 (br.s, 1H). | 92 |

TABLE 2-5

| Example No. | Compound No. | ¹H—NMR Spectrum Data(CDCl₃) δ (ppm) | Yield (%) |
|---|---|---|---|
| 26 | 1211 | 1.3–1.5(m, 3H), 1.5–1.65(m, 3H), 1.75–1.9(m, 2H), 2.0–2.15(m, 2H), 3.75(s, 2H), 3.88(s, 3H), 4.33–4.42(m, 1H), 7.02–7.15(m, 5H), 7.20–7.24(m, 1H), 7.31–7.37(m, 3H), 7.53(dt, J= 1.6 and 8.6Hz, 1H), 7.60(d, J=8.6Hz, 1H), 7.68(d, J=8.9Hz, 1H), 8.00(dd, J=1.7 and 8.2Hz, 1H), 8.72(dd, J=1.0 and 8.6Hz, 1H), 11.07(br.s, 1H). | 71 |
| 27 | 1212 | 1.25–1.65(m, 6H), 1.75–1.9(m, 2H), 2.0–2.15(m, 2H), 3.78(s, 2H), 4.31–4.40(m, 1H), 7.01–7.13(m, 6H), 7.18(dd, J=1.6 and 8.9Hz, 1H), 7.33(d, J=8.6Hz, 2H), 7.55(d, J=9.9Hz, 2H), 7.63(d, J=8.9Hz, 1H), 8.06(dd, J=1.7 and 7.9Hz, 1H), 8.75 (d, J=8.6Hz, 1H), 10.76(br.s, 1H), | 86 |
| 28 | 1213 | 0.89(t, J=6.9Hz, 3H), 1.2–1.45(m, 8H), 1.45–1.65(m, 2H), 1.84(quint, J=6.6Hz, 2H), 3.75(s, 2H), 3.88(s, 3H), 4.06 (t, J=6.6Hz, 2H), 7.03–7.15(m, 5H), 7.21–7.25(m, 1H), 7.32–7.37(m, 3H), 7.53(t, J=7.3Hz, 1H), 7.60(dd, J=2.3 and 7.6 Hz, 1H), 7.69(d, J=8.9Hz, 1H), 8.01(dd, J=1.7 and 7.9Hz, 1H), 8.73(dd, J=1.0 and 8.3Hz, 1H), 11.08(br.s, 1H). | 51 |
| 29 | 1214 | 0.85(t, J=6.6Hz, 3H), 1.25–1.55(m, 10H), 1.76(quint, J=6.6 Hz, 2H), 3.75(s, 2H), 4.05(t, J=6.6Hz, 2H), 7.01(d, J=8.6 Hz, 2H), 7.10–7.15(m, 2H), 7.23(dd, J=2.3 and 8.9Hz, 1H), 7.32–7.38(m, 4H), 7.57(t, J=7.3Hz, 1H), 7.72(d, J=9.3Hz, 1H), 7.83(d, J=8.9Hz, 1H), 7.95(dd, J=1.7 and 7.9Hz, 1H), 8.50(d, J=8.6Hz, 1H), 11.16(br.s, 1H), 13.57(br.s, 1H). (*) | 86 |
| 30 | 1215 | 2.05(s, 4H), 3.75(s, 2H), 3.89(s, 3H), 4.07(t, J=5.6Hz, 2H), 4.15(t, J=5.6Hz, 2H), 6.87–6.97(m, 3H), 7.02–7.18(m, 5H), 7.21–7.37(m, 6H), 7.50–7.57(m, 1H), 7.60(d, J=9.6Hz, 1H), 7.69(d, J=8.9Hz, 1H), 8.01(dd, J=1.6 and 7.9Hz, 1H), 8.73(dd, J=1.0 and 8.6Hz, 1H), 11.08(br.s, 1H). | 70 |

TABLE 2-6

| Example No. | Compound No. | ¹H—NMR Spectrum Data(CDCl₃) δ (ppm) | Yield (%) |
|---|---|---|---|
| 31 | 1216 | 1.8–2.0(m, 4H), 3.72(s, 2H), 4.04(t, J=5.6Hz, 2H), 4.14 (t, J=5.6Hz, 2H), 6.88–6.94(m, 3H), 7.01(d, J=8.6Hz, 2H), 7.11–7.16(m, 2H), 7.21–7.30(m, 3H), 7.35–7.38(m, 4H), 7.53–7.55(m, 1H), 7.73(d, J=8.9Hz, 1H), 7.821(d, J=8.9Hz, 1H), 7.94(dd, J=1.7 and 7.9Hz, 1H), 8.49(d, J=8.6Hz, 1H). (*) | 77 |
| 32 | 1217 | 3.75(s, 2H), 3.89(s, 3H), 4.65(d, J=6.3Hz, 2H), 5.32(d, J=10.6Hz, 1H), 5.47(d, J=17.5Hz, 1H), 6.05–6.20(m, 1H), | 47 |

TABLE 2-6-continued

| Example No. | Compound No. | $^1$H—NMR Spectrum Data(CDCl$_3$) δ (ppm) | Yield (%) |
|---|---|---|---|
| 33 | 1218 | 7.03–7.23(m, 6H), 7.32–7.37(m, 3H), 7.53(t, J=7.3Hz, 1H), 7.61(d, J=8.6Hz, 1H), 7.70(d, J=8.9Hz, 1H), 8.01(dd, J= 1.3 and 7.9Hz, 1H), 8.73(d, J=8.6Hz, 1H), 11.08(br.s, 1H), 3.74(s.2H), 4.66(d, J=5.3Hz, 2H), 5.28(dd, J=1.3 and 10.6Hz, 1H), 5.44(dd, J=1.7 and 17.5Hz, 1H), 6.03–6.15(m, 1H), 7.02(d, J=8.6Hz, 2H), 7.09–7.26(m, 3H), 7.35–7.39(m, 4H), 7.54–7.59(m, 1H), 7.74(d, J=8.9Hz, 1H), 7.83(d, J= 8.9Hz, 1H), 7.95(dd, J=1.3 and 8.2Hz, 1H), 8.50(d, J=8.6 Hz, 1H), 11.15(br.s, 1H), 13.56(br.s, 1H). (*) | 62 |
| 34 | 1219 | 1.95(quint, J=6.6Hz, 2H), 2.28(q, J=6.9Hz, 2H), 3.75(s, 2H), 3.88(s, 3H), 4.08(t, J=6.6Hz, 2H), 5.02(dd, J=2.0 and 10.3Hz, 1H), 5.09(dd, J=2.0 and 17.2Hz, 1H), 5.81–5.96 (m, 1H), 7.03–7.16(m, 5H), 7.21–7.25(m, 1H), 7.32–7.38(m, 3H), 7.53(dt, J=1.7 and 7.3Hz, 1H), 7.60(d, J=9.6Hz, 1H), 7.69(d, J=8.9Hz, 1H), 8.00(dd, J=1.7 and 7.9Hz, 1H), 8.72 (dd, J=1.3 and 8.6Hz, 1H), 11.08(br.s, 1H). | 54 |
| 35 | 1220 | 1.87(quint, J=6.3Hz, 2H), 2.23(q, J=6.6Hz, 2H), 3.76(s, 2H), 4.08(t, J=6.6Hz, 2H), 5.01(d, J=10.2Hz, 1H), 5.08 (dd, J=2.0 and 17.2Hz, 1H), 5.82–5.97(m, 1H), 7.03(d, J=8.6 Hz, 2H), 7.11–7.17(m, 2H), 7.25(dd, J=2.6 and 8.9Hz, 1H), 7.33–7.40(m, 4H), 7.58(t, J=8.6Hz, 1H), 7.74(d, J=8.9Hz, 1H), 7.85(d, J=8.9Hz, 1H), 7.96(dd, J=1.7 and 8.3Hz, 1H), 8.51(dd, J=8.3Hz, 1H), 11.14(br.s, 1H), 13.54(br.s, 1H). (*) | 89 |

TABLE 2-7

| Example No. | Compound No. | $^1$H—NMR Spectrum Data(CDCl$_3$) δ (ppm) | Yield (%) |
|---|---|---|---|
| 36 | 1221 | 1.61(s, 3H), 1.67(s, 3H), 1.78(s, 3H), 2.08–2.14(m, 4H), 3.75 (s, 2H), 3.88(s, 3H), 4.64(d, J=6.6Hz, 2H), 5.11(br., 1H), 5.56(t, J=7.6Hz, 1H), 7.03–7.07(m, 3H), 7.10–7.17(m, 2H), 7.21–7.25(m, 1H), 7.32–7.37(m, 3H), 7.53(t, J=8.6Hz, 1H), 7.60(d, J=9.6Hz, 1H), 7.70(d, J=8.9Hz, 1H), 8.01(dd, J= 1.7 and 7.9Hz, 1H), 8.72(d,m J=8.3Hz, 1H), 11.07(br.s, 1H). | 37 |
| 37 | 1222 | 1.57(s, 3H), 1.61(s, 3H), 1.74(s, 3H), 2.02–2.13(m, 4H), 3.76 (s, 2H), 4.65(d, J=6.3Hz, 2H), 5.08(br., 1H), 5.49(t, J= 6.9Hz, 1H), 7.03(d, J=8.6Hz, 2H), 7.11–7.16(m, 2H), 7.25 (dd, J=2.3 and 8.9Hz, 1H), 7.35–7.40(m, 4H), 7.58(t, J=8.6 Hz, 1H), 7.73(d, J=8.9Hz, 1H), 7.83(d, J=8.9Hz, 1H), 7.96 (d, J=1.7 and 7.9Hz, 1H), 8.51(d, J=7.9Hz, 1H), 11.14(br. s, 1H), 13.50(br.s, 1H). (*) | 66 |
| 38 | 1223 | 3.75(s, 2H), 3.88(s, 3H), 5.17(s, 2H), 7.02–7.11(m, 3H), 7.20–7.26(m, 3H), 7.32–7.56(m, 9H), 7.62(d, J=9.6Hz, 1H), 7.70(d, J=8.9Hz, 1H), 8.01(dd, J=1.7 and 8.2Hz, 1H), 8.73 (dd, J=1.0 and 8.3Hz, 1H), 11.08(br.s, 1H) | 72 |
| 39 | 1224 | 3.74(s, 2H), 5.20(s, 2H), 7.02(d,J=8.6Hz, 2H), 7.12(t, J=7.3Hz, 1H), 7.20–7.27(m, 2H), 7.30–7.58(m, 10H), 7.75 (d, J=8.9Hz, 1H), 7.83(d, J=8.9Hz, 1H), 7.95(dd, J=1.3 and 7.9Hz, 1H), 8.50(d, J=1.9Hz, 1H). (*) | 78 |
| 40 | 1225 | 2.17(quint, J=6.3Hz, 2H), 2.86(t, J=7.3Hz, 2H), 3.75(s, 2H), 3.89(s, 3H), 4.07(t, J=6.3Hz, 2H), 7.03–7.11(m, 2H), 7.05(d, J=8.6Hz, 2H), 7.13–7.38(m, 10H), 7.54(dt, J=1.7 and 7.3Hz, 1H), 7.61(d, J=8.9Hz, 1H), 7.67(d, J=8.9Hz, 1H), 8.00(dd, J=1.7 and 7.9Hz, 1H), 8.73(dd, J=1.0 and 8.6 Hz, 1H), 11.08(br.s, 1H). | 59 |

TABLE 2-8

| Example No. | Compound No. | $^1$H—NMR Spectrum Data(CDCl$_3$) δ (ppm) | Yield (%) |
|---|---|---|---|
| 41 | 1226 | 2.03–2.14(m, 2H), 2.79(t, J=7.3Hz, 2H), 3.76(s, 2H), 4.07 (t, J=6.3Hz. 2H), 7.03(d, J=8.3Hz, 2H), 7.11–7.40(m, 12H), 7.52–7.60(m, 1H), 7.75(d, J=8.9Hz, 1H), 7.83(d, J=9.2Hz, 1H), 7.96(dd, J=1.7 and 7.9Hz, 1H), 8.51(d, J=8.6Hz, 1H), 11.18(br.s, 1H). (*) | 86 |
| 42 | 1227 | 3.75(s, 2H), 3.88(s, 3H), 5.34(s, 2H), 7.03–7.10(m, 3H), 7.22–7.28(m, 3H), 7.33–7.37(m, 3H), 7.46–7.71(m, 6Hz, 7.84–7.90(m, 3H), 7.94(s, 1H), 8.00(dd, J=1.7 and 7.9Hz, 1H), 8.72(d, J=8.6Hz, 1H), 11.07(br, s, 1H). | 23 |
| 43 | 1228 | 3.76(s, 2H), 5,39(s, 2H), 7.03(d, J=8.6Hz, 2H), 7.14(d, J= 7.9Hz, 1H), 7.24–7.30(m, 2H), 7.38(d, J=8.6Hz, 3H), 7.51– | 30 |

TABLE 2-8-continued

| Example No. | Compound No. | ¹H—NMR Spectrum Data(CDCl₃) δ (ppm) | Yield (%) |
|---|---|---|---|
| | | 7.66(m, 5H), 7.78(d, J=9.2Hz, 1H), 7.86(d, J=8.9Hz, 1H), 7.93–7.98(m, 4H), 8.05(s, 1H), 8.51(d, J=7.9Hz, 1H), 11.17(br.s, 1H), 13.56(br.s, 1H). (*) | |
| 44 | 1149 | 1.64(d, J=7.3Hz, 3H), 3.75–3.83 (m, 4H), 3.89(s, 3H), 7.03–7.09(m, 3H), 7.24–7.28(m, 1H), 7.33–7.56(m, 6H), 7.69(dd, J= 1.7 and 7.6Hz, 1H), 7.81(d, J=8.9Hz, 2H), 8.00(dd, J=1.7 and 7.9Hz, 1H), 8.74(dd, J=1.0 and 8.6Hz, 1H), 11.14(br.s, 1H), | 65 |
| 45 | 1150 | 1.48(d, J=6.9Hz, 3H), 3.88(q, J=6.9Hz, 1H), 7.04–7.14(m, 3H), 7.28(dd, J=2.3 and 8.9Hz, 1H), 7.39–7.59(m, 6H), 7.80 (d, J=7.6Hz, 1H), 7.90(dd, J=1.3 and 7.6Hz, 1H), 7.95(d, J=8.2Hz, 2H), 8.52(d, J=7.6Hz, 1H), 11.28(br.s, 1H). (*) | 71 |
| 46 | 1151 | 1.73(s, 6H), 3.84(s, 3H), 7.07(d, J=8.9Hz, 3H), 7.25–7.29 (m, 1H), 7.34–7.56(m, 6H), 7.68(d, J=7.9Hz, 1H), 7.81(d, J=8.9Hz, 2H), 7.99(dd, J=1.7 and 7.9Hz, 1H), 8.76(dd, J=1.0 and 7.6Hz, 1H), 10.95(br.s, 1H). | 88 |

TABLE 2-9

| Example No. | Compound No. | ¹H—NMR Spectrum Data(CDCl₃) δ (ppm) | Yield (%) |
|---|---|---|---|
| 47 | 1152 | 1.61(s, 6H), 7.07(d, J=8.6Hz, 2H), 7.11(t, J=7.3Hz, 1H), 7.28(dd, J=1.6 and 8.9Hz, 1H), 7.40–7.52(m, 5H), 7.58(dt, J= 1.7 and 6.9Hz, 1H), 7.80(d, J=7.9Hz, 1H), 7.90–7.97(m, 3H), 8.62(d, J=8.6Hz, 1H), 11.25(br.s, 1H), 13.62(br.s, 1H). (*) | 85 |
| 48 | 1153 | 2.36(s, 3H), 3.88(s, 3H), 7.14(d, J=8.9Hz, 2H), 7.18–7.24 (m, 1H), 7.27–7.31(m, 1H), 7.42–7.53(m, 4H), 7.76(d, J=7.3 Hz, 1H), 7.84–7.91(m, 3H), 8.01–8.04(m, 2H), 10.18(br.s, 1H). | 50 |
| 49 | 1154 | 2.36(s, 3H), 7.13(d, J=8.6Hz, 2H), 7.21–7.30(m, 2H), 7.43 7.55(m, 4H), 7.76(d, J=7.3Hz, 1H), 7.85–7.94(m, 3H), 8.00 (d, J=8.9Hz, 2H), 9.98(br.s, 1H). | 71 |
| 50 | 1155 | 3.80(s, 2H), 3.95(s, 3H), 7.10(d, J=6Hz, 2H), 7.26–7.46 (m, 6H), 7.69(d, J=9Hz, 1H), 7.82(d, J=9Hz, 2H), 7.87 (dd, J=2 and 9Hz, 1H), 8.17(d, J=9Hz, 1H), 9.64(d, J= 2Hz, 1H), 11.12(br.s, 1H). | 53 |
| 51 | 1156 | 3.83(s, 2H), 7.08(d, J=8Hz, 2H), 7.29(dd, J=2 and 9Hz, 1H), 7.39–7.48(m, 5H), 7.81(d, J=8Hz, 1H), 7.89–7.97(m, 3H), 8.19(d, J=9Hz, 1H), 9.37(d, J=2Hz, 1H), 11.65 (br.s, 1H). (*) | 69 |
| 52 | 1157 | 3.77(s, 2H), 3.88(s, 3H), 6.77(d, J=2 and 7Hz, 1H), 7.08 (d, J=9Hz, 2H), 7.32–7.48(m, 6H), 7.69(d, J=8Hz, 1H), 7.82(d, J=9Hz, 2H), 8.02(dd, J=6 and 9Hz, 1H), 8.57(dd, J=3 and 12Hz, 1H), 11.25(br.s, 1H). | 62 |
| 53 | 1158 | 3.78(s, 2H), 6.68(m, 1H), 7.11(d, J=9Hz, 2H), 7.20(dd, J= 2 and 9Hz, 2H), 7.32–7.42(m, 4H), 7.61(d, J=8Hz, 1H), 7.75(d, J=9Hz, 2H), 8.05(t, J=6Hz, 1H), 8.56(dd, J=2 and 12Hz, 1H), 10.88(br.s, 1H). | 82 |

TABLE 2-10

| Example No. | Compound No. | ¹H—NMR Spectrum Data(CDCl₃) δ (ppm) | Yield (%) |
|---|---|---|---|
| 54 | 1159 | 3.76(s, 2H), 3.89(s, 3H), 7.09(d, J=9Hz, 2H), 7.26–7.45 (m, 7H), 7.68(dd, J=3 and 9Hz, 2H), 7.82(d, J=9Hz, 2H), 8.74(dd, J=5 and 9Hz, 1H), 10.91(br.s, 1H). | 60 |
| 55 | 1160 | 3.75(s, 2H), 7.07(d, J=9Hz, 2H), 7.29(dd, J=3 and 9Hz, 1H), 7.38–7.48(m, 6H), 7.54(dd, J=3 and 9Hz, 1H), 7.82(d, J=8Hz, 1H), 7.88–7.91(m, 1H), 7.95(d, J=9Hz, 1H), 8.52 (d, J=9Hz, 1H), 11.99(br.s, 1H). (*) | 85 |
| 56 | 1161 | 3.76(s, 2H), 3.89(s, 3H), 7.09(d, J=9Hz, 2H), 7.25–7.51 (m, 7H), 7.69(d, J=8Hz, 1H), 7.82(d, J=9Hz, 2H), 7.98(d, J=3Hz, 1H), 8.73(d, J=9Hz, 1H), 10.99(br.s, 1H). | 95 |
| 57 | 1162 | 3.71(s, 2H), 7.06(d, J=9Hz, 2H), 7.29(dd, J=3 and 9Hz, 2H), 7.38–7.50(m, 5H), 7.67(dd, J=3 and 10Hz, 1H), 7.82(d, J=8Hz, 1H), 7.89(d, J=8Hz, 1H), 7.95(d, J=9Hz, 1H), 8.50(dd, J=5 and 9Hz, 1H), 12.3(br.s, 1H). (*) | 81 |
| 58 | 1163 | 2.41(s, 3H), 3.73(s, 2H), 3.81(s, 3H), 6.96(d, J=8Hz, 1H), 7.10(d, J=9Hz, 2H), 7.27–7.46(m, 7H), 7.70(d, J= 7Hz, 1H), 7.82(dd, J=3 and 9Hz, 2H), 8.23(d, J=9Hz, 1H), 9.39(br.s, 1H). | 38 |
| 59 | 1164 | 2.37(s, 3H), 3.65(s, 2H), 6.96(d, J=7Hz, 1H), 7.04(d, J= | 75 |

TABLE 2-10-continued

| Example No. | Compound No. | $^1$H—NMR Spectrum Data(CDCl$_3$) δ (ppm) | Yield (%) |
|---|---|---|---|
| | | 8Hz, 2H), 7.17–7.49(m, 7H), 7.73(d, J=8Hz, 1H), 7.81(d, J=8Hz, 1H), 7.90(d, J=8Hz, 1H), 7.94(d, J=8Hz, 1H), 10.57(br.s, 1H). (*) | |

TABLE 2-11

| Example No. | Compound No. | $^1$H-NMR Spectrum Data (CDCl$_3$) δ (ppm) | Yield (%) |
|---|---|---|---|
| 60 | 4101 | 3.92(s, 3H), 4.20(s, 2H), 7.09(t, J=7.3Hz, 1H), 7.22–7.48(m, 5H), 7.56–7.64(m, 2H), 7.76–7.82(m, 3H), 7.99(d, J=7.9Hz, 2H), 8.06(dd, J=1.3 and 8.3Hz, 1H), 8.93(d, J=8.6Hz, 1H), 12.01(br, s, 1H). | 100 |
| 61 | 4103 | 4.22(s, 2H), 7.15(t, J=8.3Hz, 1H), 7.24–7.50(m, 5H), 7.63–7.69(m, 2H), 7.77–7.83(m, 3H), 7.96(d, J=8.6Hz, 2H), 8.14(dd, J=1.7 and 7.9Hz, 1H), 8.96(d, J=7.9Hz, 1H), 11.80(br, s, 1H). | 79 |
| 62 | 5101 | 3.95(s, 3H), 5.26(s, 2H), 7.09–7.15(m, 1H), 7.20–7.27(m, 2H), 7.34(dt, J=1.3 and 7.9Hz, 1H), 7.44(dt, J=1.3 and 7.9Hz, 1H), 7.57–7.65(m, 3H), 7.72(d, J=8.3Hz, 1H), 7.77(d, J=8.6Hz, 2H), 8.06–8.11(m, 3H), 8.94(d, J=8.3Hz, 1H), 12.07(br, s, 1H). | 60 |
| 63 | 5102 | 5.28(s, 2H), 7.17–7.45(m, 5H), 7.63–7.80(m, 6H), 8.07(d, J=8.6Hz, 2H), 8.15(dd, J=1.7 and 7.9Hz, 1H), 8.95–8.99(m, 1H), 11.90(s, 1H). | 85 |

TABLE 2-12

| Example No. | Compound No. | $^1$H-NMR Spectrum Data (CDCl$_3$) δ (ppm) | Yield (%) |
|---|---|---|---|
| 64 | 5103 | 3.78(s, 2H), 3.85(s, 3H), 5.18(s, 2H), 7.06(t, J=7.9Hz, 1H), 7.19–7.23(m, 2H), 7.30–7.36(m, 1H), 7.40–7.55(m, 6H), 7.70–7.78(m, 3H), 7.99(dd, J=1.7 and 8.2Hz, 1H), 8.70(d, J=8.3Hz, 1H), 11.10(br, s, 1H). | 65 |
| 65 | 5104 | 3.81(s, 2H), 5.19(s, 2H), 6.98(t, J=7.9Hz, 1H), 7.16–7.21(m, 2H), 7.30–7.45(m, 4H), 7.50–7.56(m, 3H), 7.65–7.77(m, 3H), 8.03(dd, J=1.7 and 7.9Hz, 1H), 8.74(dd, J=1.0 and 8.6Hz, 1H), 10.68(br, s, 1H). | 76 |
| 66 | 6101 | 3.96(s, 3H), 4.26(s, 2H), 7.12(dt, J=1.3 and 8.3Hz, 1H), 7.38–7.50(m, 5H), 7.60(dt, J=1.7 and 8.6Hz, 1H), 7.69–7.80(m, 4H), 7.95(d, J=2.0Hz, 1H), 7.98(d, J=1.7Hz, 1H), 8.08(dd, J=1.7 and 7.9Hz, 1H), 8.92(d, J=8.6Hz, 1H), 12.01(br, s, 1H). | 87 |
| 67 | 6102 | 4.26(s, 2H), 7.15(t-like, 1H), 7.29–7.47(m, 5H), 7.63–7.80(m, 5H), 7.92–7.95(m, 2H), 8.13(dd, J=1.7 and 7.9Hz, 1H), 8.93–8.96(m, 1H), 11.84(s, 1H). | 22 |
| 68 | 7101 | 3.99(s, 3H), 7.17(t, J=8.6Hz, 1H), 7.55–7.68(m, 3H), 7.92–8.02(m, 6H), 8.12(dd, J=1.3 and 7.9Hz, 1H), 8.18–8.28(m, 3H), 8.96(d, J=8.6Hz, 1H), 12.21(br, s, 1H). | 79 |
| 69 | 7102 | 7.18–7.24(m, 1H), 7.58–7.70(m, 3H), 7.92–8.01(m, 6H), 8.17(d, J=8.6Hz, 3H), 8.28(s, 1H), 8.99(d, J=8.3Hz, 1H), 12.04(br, s, 1H). | 79 |

TABLE 2-13

| Example No. | Compound No. | $^1$H-NMR Spectrum Data (CDCl$_3$) δ (ppm) | Yield (%) |
|---|---|---|---|
| 70 | 7103 | 3.96(s, 3H), 7.15(t, J=7.3Hz, 1H), 7.50–7.70(m, 5H), 7.90–8.20(m, 8H), 8.92(d, J=7.6Hz, 1H), 12.1(s, 1H). | 90 |
| 71 | 7104 | 7.24(t, J=7.3Hz, 1H), 7.50–7.70(m, 5H), 7.95(d, J=8.3Hz, 2H), 8.00–8.10(m, 5H), 8.11(d, J=1.7Hz, 1H), 8.68(d, J=8.3Hz, 1H), 12.3(s, 1H), 13.8(br, s, 1H). (*) | 69 |
| 72 | 8101 | 3.45(s, 3H), 3.94(s, 3H), 5.47(s, 1H), 7.11(t, J=7.3Hz, 1H), 7.41–7.52(m, 3H), 7.55–7.64(m, 3H), 7.73–7.85(m, 4H), 8.00–8.09(m, 3H), 8.92(d, J=8.3Hz, 1H), 12.01(br, s, 1H). | 100 |

TABLE 2-13-continued

| Example No. | Compound No. | $^1$H-NMR Spectrum Data (CDCl$_3$) δ (ppm) | Yield (%) |
|---|---|---|---|
| 73 | 8102 | 3.45(s, 3H), 5.48(s, 1H), 7.15(t, J=7.3Hz, 1H), 7.40–7.68(m, 6H), 7.80–7.85(m, 4H), 8.00(d, J=8.2Hz, 2H), 8.14(d, J=7.9Hz, 1H), 8.95(d, J=8.6Hz, 1H), 11.82(br, s, 1H). | 80 |

Example 74

Production of N-phenyl-4-(2-naphtyloxy)benzamide (Compound No. 1105)

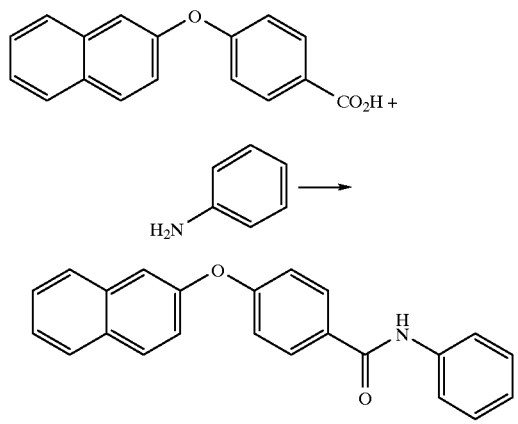

Under an atmosphere of nitrogen, 53 mg (0.20 mmol) of 4-(2-naphtyloxy) benzoic acid was suspended in 5 ml of dried methylene chloride, to which were added 56 mg (0.44 mmol) of oxyalyl chloride and then 1 drop of DMF with a pipette. The mixture was stirred at 35° C. for 1.5 hours. The reaction mixture was concentrated with an evaporator, and the residue was dissolved in 5 ml of dried methylene chloride. Under an atmosphere of nitrogen, the solution, while being cooled with ice, was added dropwise to a solution of 19 mg (0.20 mmol) of aniline and of 22 mg (0.22 mmol) of triethyl amine in dried methylene chloride (5 ml), and the resulting mixture was stirred for 4 hours in an ice bath, and then stirred overnight at room temperature. Water was added to the reaction mixture, and extracted with methylene chloride twice. The organic phase was washed with brine dried with anhydrous sodium sulfate, and the solvent was removed by evaporation. The residue was purified by silica gel column chromatography (hexane:ethyl acetate=20:1) to give 27 mg (40% yield) of N-phenyl-( 4-(2-naphtyloxy)benzamide). White solid.

$^1$H-NMR (CDCl$_3$) δ (ppm): 7.10–7.18(m, 3H), 7.24–7.29 (m, 2H), 7.34–7.53(m, 4H), 7.62–7.65(m, 2H), 7.74–7.77 (m, 2H), 7.86–7.90(m, 3H).

Example 75

Production of 2-(4-(2-naphtyloxy)benzamide)phenol (Compound No. 1106)

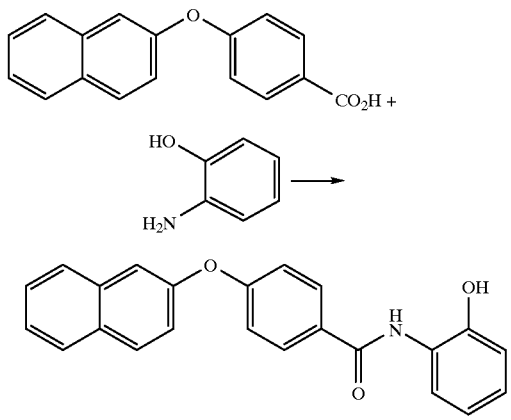

Under an atmosphere of nitrogen, 144 mg (0.54 mmol) of 4-(2-naphtyloxy)benzoic acid was suspended in 5 ml of dried methylene chloride, to which were added 76 mg (0.60 mmol) of oxyalyl chloride and then 1 drop of DMF with a pipette. The mixture was stirred at 35° C. for 1.5 hours. The reaction mixture was concentrated with an evaporator, and the residue was dissolved in 9 ml of dried methylene chloride. Under an atmosphere of nitrogen, the solution, while being cooled with ice, was added dropwise to a solution of 59 mg (0.54 mmol) of o-aminophenol and of 3 ml of dried pyridine in dried methylene chloride (6 ml), and the resulting mixture was stirred for 1.5 hours in an ice bath, and then stirred at room temperature for three days. Water was added to the reaction mixture, and extracted with methylene chloride twice. The organic phase was washed with brine, and dried with anhydrous sodium sulfate, and the solvent was removed by evaporation. The residue was purified through silica gel chromatography (hexane:ethyl acetate=20:1 to 10:1) to give 147 mg (76% yield) of 2-(4-(2-naphthyloxy)benzamide)phenol. White solid.

$^1$H-NMR (CDCl$_3$) δ (ppm): 6.89–6.96(m, 1H), 7.03–7.23 (m, 5H), 7.28–7.29(m, 1H), 7.44–7.76(m, 3H) , 7.78–7.79(d, J=1.7Hz, 1H), 7.85–7.94(m, 4H), 8.67(s, 1H).

Example 76

Production of 2-(4-(2-naphtyloxy)benzamide)benzenesulfonamide (Compound No. 1107)

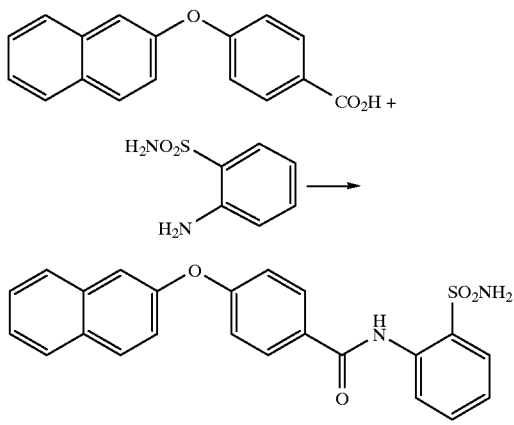

Under an atmosphere of nitrogen, 132 mg (0.5 mmol) of 4-(2-naphtyloxy)benzoic acid was suspended in 5 ml of dried methylene chloride, to which were added 70 mg (0.55 mmol) of oxyalyl chloride and then 1 drop of DMF with a pipette. The mixture was stirred at 35° C. for 2 hours. The reaction mixture was concentrated with an evaporator, and the residue was dissolved in 5 ml of dried methylene chloride. In an atmosphere of nitrogen, the solution, while being cooled with ice, was added dropwise to a solution of 86 mg (0.5 mmol) of o-aminobenzenesulfonamide and of 2 ml of dried pyridine in dried methylene chloride (4 ml), and the resulting mixture was stirred for 4 hours in an ice bath, and then stirred overnight at room temperature. Water was added to the reaction mixture, and extracted with methylene chloride twice. The organic phase was washed with brine, dried with anhydrous sodium sulfate, and the solvent was removed by evaporation. The residue was recrystallized from a mixed solvent of isopropyl/ethyl acetate (8 ml/3 ml) to give 112 mg (54% yield) of 2-(4-(2-naphthyloxy)benzamide)benzene sulfonamide. White granular crystals.

$^1$H-NMR (DMSO-d$_6$) δ (ppm): 7.23(d, J=8.9Hz, 2H), 7.26–7.38(m, 2H), 7.46–7.68(m, 4H), 7.90(d, J=7.9Hz, 2H), 7.97(d, J=8.6Hz, 3H), 8.04(d, J=9.2Hz, 1H), 8.46(dd, J=1.0 and 8.6Hz, 1H).

Example 77

Production of 2-(4-(2-naphtyloxy)benzamide)benzonitrile (Compound No. 1108)

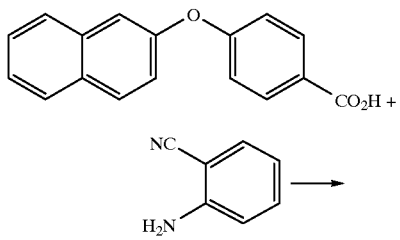

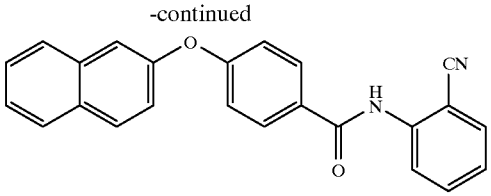

Under an atmosphere of nitrogen, 264 mg (1.0 mmol) of 4-(2-naphtyloxy)benzoic acid was suspended in 5 ml of dried methylene chloride, to which were added 140 mg (1.1 mmol) of oxyalyl chloride and then 1 drop of DMF with a pipette. The mixture was stirred at 35° C. for 2 hours. The reaction product was concentrated with an evaporator, and the residue was dissolved in 7 ml of dried methylene chloride. In an atmosphere of nitrogen, the solution, while being cooled with ice, was added dropwise to a solution of 118 mg (1.0 mmol) of anthranilonitrile and of 111 mg (1.1 mmol) of triethyl amine in dried methylene chloride (5 ml), and the resulting mixture was stirred for 4 hours in an ice bath, and then stirred overnight at room temperature. Water was added to the reaction mixture, and extracted with methylene chloride twice. The organic phase was washed with brine, dried with anhydrous sodium sulfate, and the solvent was removed by evaporation. The residue purified by silica gel-column chromatography (hexane:ethyl acetate=20:1 to 5:1) to give 263 mg (72% yield) of 2-(4-(2-naphthyloxy)benzamide) benzonitrile. White solid.

$^1$H-NMR (CDCl$_3$) δ (ppm): 7.15(d, J=8.9Hz, 2H), 7.18–7.30(m, 2H), 7.46–7.54(m, 3H), 7.61–7.69(m, 2H), 7.76–7.79(m, 1H), 7.85–7.96(m, 4H), 8.34(br, s, 1H), 8.61 (d, J=8.6Hz, 1H).

Example 78

Production of 2-(4-(2-naphtylthio)benzamide)benzonitrile (Compound No. 3103)

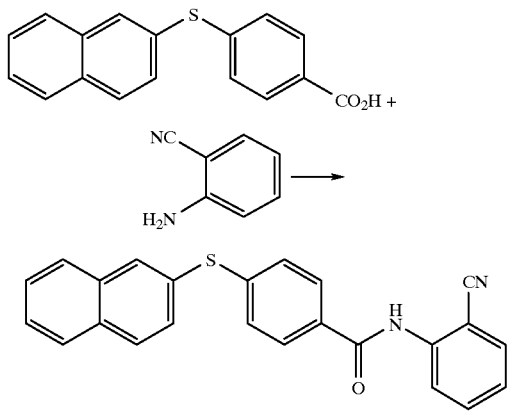

A 280 mg (1.0 mmol) of 4-(2-naphtylthio)benzoic acid was used as a starting material. 104 mg of the title compound was prepared according to the procedure in Example 77 (yield 27%).

$^1$H-NMR (CDCl$_3$) δ (ppm): 7.21(t, J=8.6Hz, 1H), 7.33(d, J=8.6Hz, 2H), 7.49–7.68(m, 4H), 7.78–7.89(m, 4H), 8.06(d, J=1.3Hz, 1H), 8.31(br, s, 1H), 8.59(d, J=8.6Hz, 1H).

Example 79

Production of 1-(4-(2-naphtyloxy)benzamide)-2-(tetrazol-5-yl)benzene (Compound No. 1109)

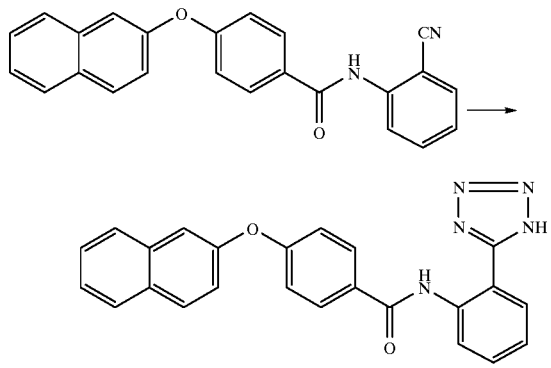

A 109 mg (0.30 mmol) of 2-(4-(2-naphtyloxy)benzamide)benzonitrile (Compound No. 1108), 48 mg (0.9 mmol) of ammonium chloride and 59 mg (0.9 mmol) of sodium azide were suspended in 3 ml of dried DMF, and the suspension was stirred at 80° C. for 24 hours. To the reaction mixture were added 5 ml of water and 5 ml of 5 N hydrochloric acid, and to the resulting mixture was extracted with ethyl acetate twice. The organic phase was washed with brine, dried with anhydrous sodium sulfate, and the solvent was removed by evaporation. The residue was recrystallized from 15 ml of acetonitrile to give 92 mg (75% yield) of 1-(4-(2-naphthyloxy)benzamide)-2-(tetrazol-5-yl)benzene. White needle-like crystals.

$^1$H-NMR (CDCl$_3$) δ (ppm): 7.15–7.21(m, 2H), 7.27–7.35 (m, 2H), 7.43–7.53(m, 3H), 7.57–7.63(m, 1H), 7.78–8.01 (m, 4H), 8.14–8.19(m, 2H), 8.76–8.81(m, 1H).

Example 80

Production of 1-(4-(2-naphtylthio)benzamide)-2-(tetrazol-5-yl)benzene (Compound No. 3104)

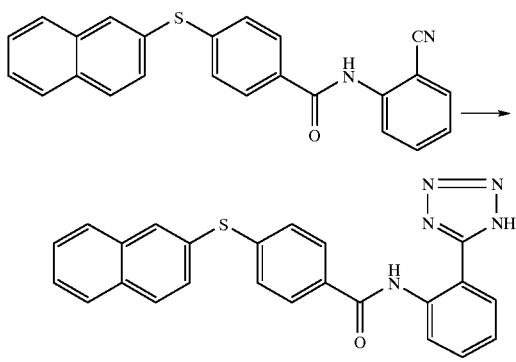

A 50 mg (0.13 mmol) of 2-4-(2-naphtylthio)benzamide)benzonitrile (Compound No. 3103) obtained in Example 78 was used as a starting material. 43 mg of the title compound was prepared according to the procedure in Example 79 (yield 77%).

$^1$H-NMR (DMSO-d$_6$) δ (ppm): 7.42(t, J=8.6Hz, 1H), 7.48(d, J=8.3Hz, 2H), 7.57–7.70(m, 4H), 8.00–8.09(m, 6H), 8.24(d, J=1.7Hz, 1H), 8.57(d, J=7.6Hz, 1H). 11.56(br, s, 1H).

Example 81

Production of 2-(3-amino-4-(2-naphtyloxy)benzamide)benzoic Acid Methyl Ester (Compound No. 1117)

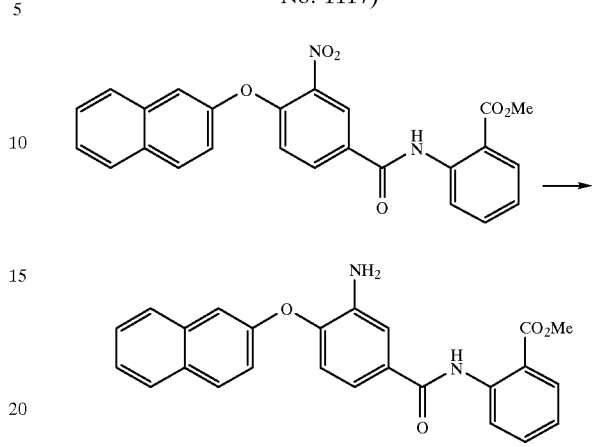

A 350 mg (0.79 mmol) of 2-(4-(2-naphtyloxy)-3-nitrobenzamide)benzoic acid methyl ester (Compound No. 1114) obtained in Example 7 was dissolved in 20 ml of ethyl acetate, to which was added 97 mg of 10% Pd/C. The system was put in an atmosphere of hydrogen, and stirred at room temperature for 4 hours. The reaction mixture was filtered through a sheet of celite and the filtrate was concentrated. The residue was purified by silica gel column chromatography (hexane:ethyl acetate=4:1 to 2:1) to give 200 mg (61% yield) of 2-(3-amino-4-(2-naphthyloxy)benzamide)benzoic acid.

$^1$H-NMR (CDCl$_3$) δ (ppm): 3.95(s, 3H), 6.95(d, J=8.5Hz, 1H), 7.11(t, J=7.0Hz, 1H), 7.30(dd, J=2.3 and 8.9Hz, 2H), 7.36(dd, J=2.3 and 8.2Hz, 2H), 7.40–7.50(m, 3H), 7.57(d, J=2.0Hz, 1H), 7.61(dd, J=1.4 and 8.6Hz, 1H), 7.71(d, J=7.9Hz, 1H), 7.84(t, J=8.0Hz, 2H), 8.07(dd, J=1.5 and 8.7Hz, 1H), 8.92(d, J=1.3 and 8.3Hz, 1H), 11.9(s, 1H).

Example 82

Production of 2-(3-amino-4-(2-naphtyloxy)benzamide)benzoic Acid (Compound No. 1118)

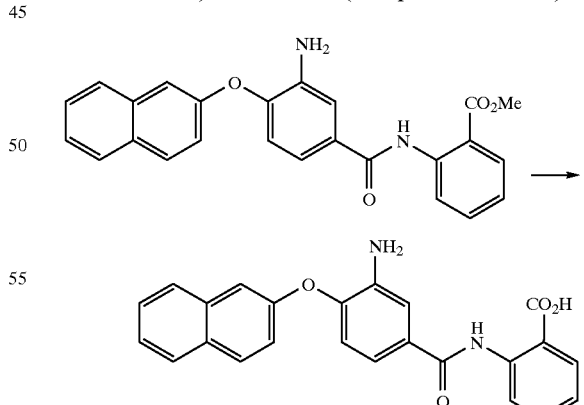

A 200 mg (0.48 mmol) of 2-(3-amino-4-(2-naphtyloxy)benzamide) benzoic acid methyl ester (Compound No. 1117) obtained in Example 81 was used as a starting material. 51 mg of the title compound was prepared according to the procedure in Example 2 (Yield 26%).

¹H-NMR (DMSO-d₆) δ (ppm): 5.40(br, s, 2H), 6.96(d, J=7.8Hz, 1H), 7.10–7.30(m, 2H), 7.30–7.35(m, 2H), 7.40–7.50(m, 3H), 7.63(dt, J=1.5 and 7.6Hz, 1H), 7.82(d, J=7.8Hz, 1H), 7.90(d, J=7.8Hz, 1H), 7.96(d, J=9.8Hz, 1H), 8.05(dd, J=1.5 and 7.8Hz, 1H), 8.73(d, J=7.8Hz, 1H), 12.2(s, 1H).

Example 83

Production of the Sodium Salt of 2-(4-(2-naphtyloxy)benzamide)benzoic Acid-Ethanol Complex. (Compound No. 1104)

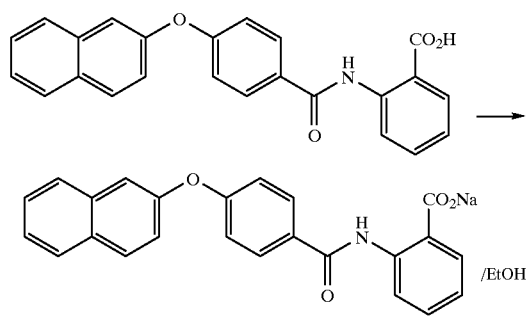

A 10.35 g (27.0 mmol) of 2-(4-(2-naphtyloxy)benzamide)benzoic acid (Compound No. 1104) obtained in Example 2 was dissolved in 250 ml of ethanol under heating, to which was added 13.77 ml (27.54 mmol) of 2 N sodium hydroxide. The resulting mixture was stirred at room temperature for 10 minutes and allowed to stand overnight. White crystallized solids were filtered to give 10.15 g (yield 83%) of the compound indicated in the title.

¹H-NMR (DMSO-d₆) δ (ppm): 1.07(t, J=6.9Hz, 3H), 3.44–3.47(m, 2H), 4.30–4.32(m, 1H), 6.97(t, J=7.5Hz, 1H), 7.17(d, J=7.5Hz, 2H), 7.30(t, J=6.9Hz, 1H), 7.35(d, J=8.5Hz, 1H), 7.47–7.55(m, 3H), 7.87(d, J=8.0Hz, 1H), 7.94(d, J=8.0Hz, 1H), 8.02(t, J=8.0Hz, 2H), 8.09(d, J=8.5Hz, 2H), 8.69(d, J=8.0Hz, 1H), 15.66 (br, s, 1H).

Example 84

Production of the Lysine Salt of 2-(4-(2-naphtyloxy)benzamide)benzoic Acid (Compound No. 1104)

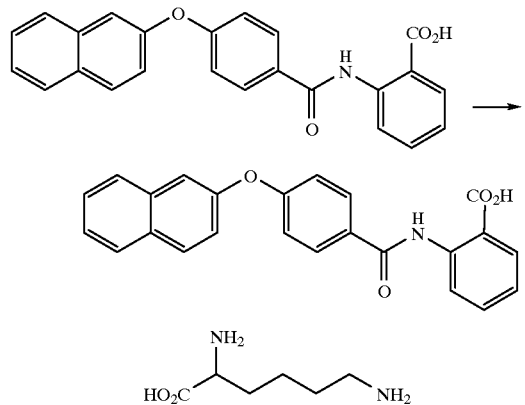

A 192 mg (0.5 mmol) of 2-(4-(2-naphtyloxy)benzamide)benzoic acid (Compound No. 1104) obtained in Example 2 was dissolved in ethanol (6 ml) to which was added 3 ml of methanol solution of 73 mg (0.5 mmol) of 1-lysine free base. The resulting mixture was stirred at room temperature for 5 minutes, and allowed to stand for 6 hours. White crystallized solid was filtered to give 247 mg (93% recovery) of the compound indicated in the title.

¹H-NMR (CDCl₃-CD₃OD) (ppm): 1.40–1.58(m, 2H), 1.58–1.73(m, 2H), 1.78–1.90(m, 2H), 2.86–2.97(m, 2H), 3.50–3.60(m, 1H), 7.03–7.19(m, 3H), 7.23–7.32(m, 1H), 7.39–7.53(m, 4H), 7.75–7.83(m, 1H), 7.83–7.98(m, 2H), 8.05–8.17(m, 3H), 8.65–8.73(m, 1H).

Example 85

Production of the N-methyl-D-glucamine Salt of 2-(4-(2-naphtyloxy)benzamide)benzoic Acid (Compound No. 1104)

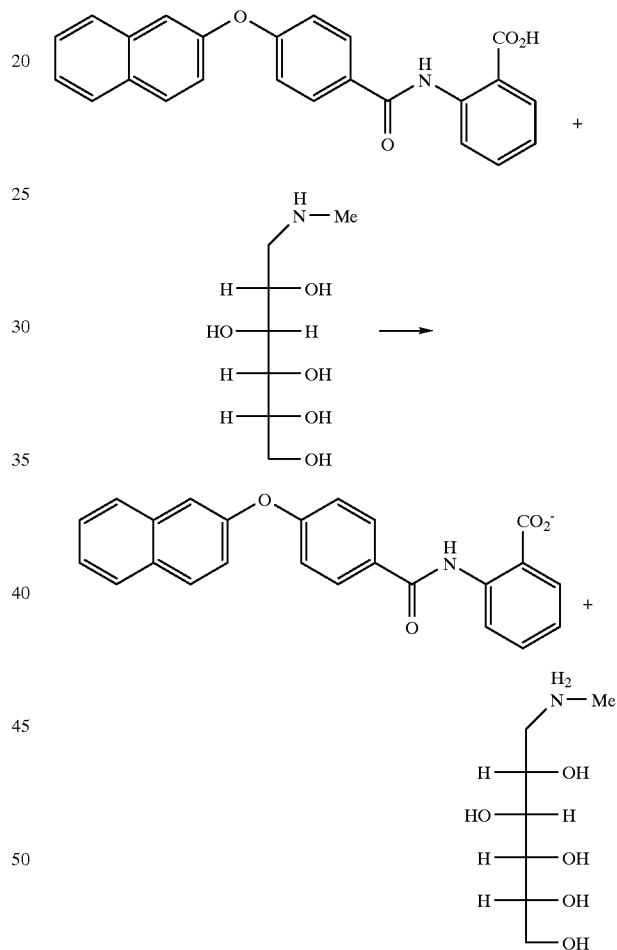

A 383 mg (1.0 mmol) of 2-(4-(2-naphtyloxy)benzamide)benzoic acid (Compound No. 1104) obtained in Example 2 was dissolved in ethanol (12 ml), to which was added 1 ml of aqueous solution of 195 mg (1.0 mmol) of N-methyl-D-glucamine. The resulting mixture was stirred at room temperature for 1 hour. The reaction product was filtered through a glass filter to remove a faint amount of impurities, and the filtrate concentrated. The residue (a viscid liquid) was dissolved in a mixed solvent comprising 20 ml of water and 1 ml of methanol, and the mixture was lyophilized to give 542 mg (yield 94%) of the compound indicated in the title in the form of white powder.

$^1$H-NMR (DMSO-$d_6$) δ (ppm): 2.49–2.51(m, 5H), 2.89–3.07(m, 2H), 3.38–3.47(m, 3H), 3.57–3.61(m, 1H), 3.66–3.67(m, 1H), 3.86(br, s, 1H), 4.40–4.44(br, s, 1H), 4.58(br, s, 1H), 5.43(br, s, 1H), 6.98(t, J=8.6Hz, 1H), 7.20(d, J=8.9Hz, 2H), 7.22–7.39(m, 2H), 7.45–7.57(m, 3H), 7.87–8.09(m, 6H), 8.64(d, J=8.3Hz, 1H).

Example 86

Production of the Sodium Salt of 1-(4-(2-naphtyloxy)benzamide)-2-(tetrazol-5-yl)benzene (Compound No. 1109)

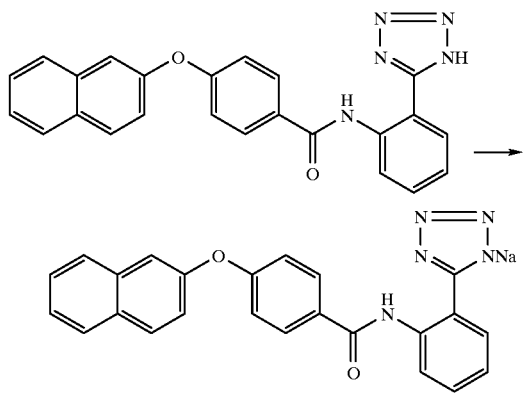

A 732 mg (1.80 mmol) of 1-(4-(2-naphtyloxy)benzamide)-2-(tetrazol-5-yl)benzene (Compound No. 1109) obtained in Example 79 was dissolved in 80 ml of ethanol under heating, to which was added 0.897 ml (1.80 mmol) of 2 N sodium hydroxide aqueous solution. The resulting mixture was stirred at room temperature for 2.5 hours. The reaction mixture was concentrated and the residue (a clear film) was dissolved in 30 ml of distilled water. The resulting solution was filtered through a filter (0.45 μm), and the filtrate was lyophilyzed to give 767 mg (yield 99%) of the compound indicated in the title in the form of white powder.

$^1$H-NMR (DMSO-$d_6$) (ppm): 7.15(td, J=1.5 and 7.8Hz, 1H), 7.25(dt, J=2.9 and 8.8Hz, 2H), 7.31(td, J=1.5 and 8.8Hz, 1H), 7.39(dd, J=2.5 and 8.8Hz, 1H), 7.47–7.54(m, 2H), 7.60(d, J=2.4Hz, 1H), 7.90(d, J=7.8Hz, 1H), 7.90(d, J=7.8Hz, 1H), 7.96(d, J=7.8Hz, 1H), 8.03(d, J=9.3Hz, 1H), 8.25–8.30(m, 3H), 8.79(dd, J=1.0 and 8.3Hz, 1H), 13.39(br, s, 1H).

Example 87

Production of the Sodium Salt of 2-(4-(2-naphtyloxy)phenylacetamide)benzoic Acid (Compound No. 1126)

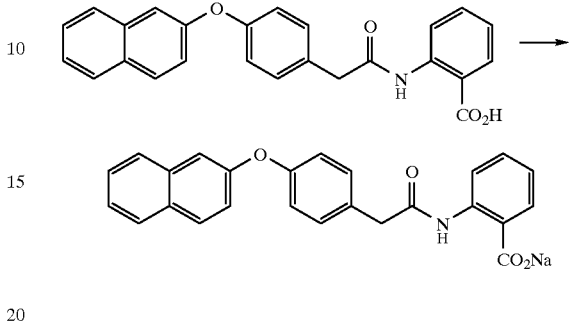

A 9.538 g (24.00 mmol) of 2-(4-(2-naphtyloxy)phenylacetamide)benzoic acid (Compound No. 1126) obtained in Example 13 was dissolved in 100 ml of ethanol under heating, to which was added 11.976 ml (24.00 mmol) of 2 N sodium hydroxide aqueous solution. The resulting mixture was stirred at room temperature for 1.5 hours. The reaction mixture was concentrated and the residue (a clear film) was dissolved in 200 ml of distilled water. The resulting solution was filtered through a filter (0.45 μm), and the filtrate was lyophilized to give 9.97 g (yield 99%) of the compound indicated in the title in the form of white powder.

$^1$H-NMR (DMSO-$d_6$) δ (ppm): 3.65(s, 2H), 6.95(t, J=8.2Hz, 1H), 7.10(d, J=8.6Hz, 2H), 7.25(t, J=7.3Hz, 1H), 7.33–7.36(m, 1H), 7.37–7.53(m, 5H), 7.93(t, J=7.3Hz, 2H), 7.99(d, J=8.9Hz, 2H), 8.46(d, J=8.3Hz, 1H), 14.80–14.91 (m, 1H).

Example 88

Production of 2-(4-(6-hydroxy-2-naphtyloxy)benzamide)benzoic Acid Methyl Ester (Compound No. 1201)

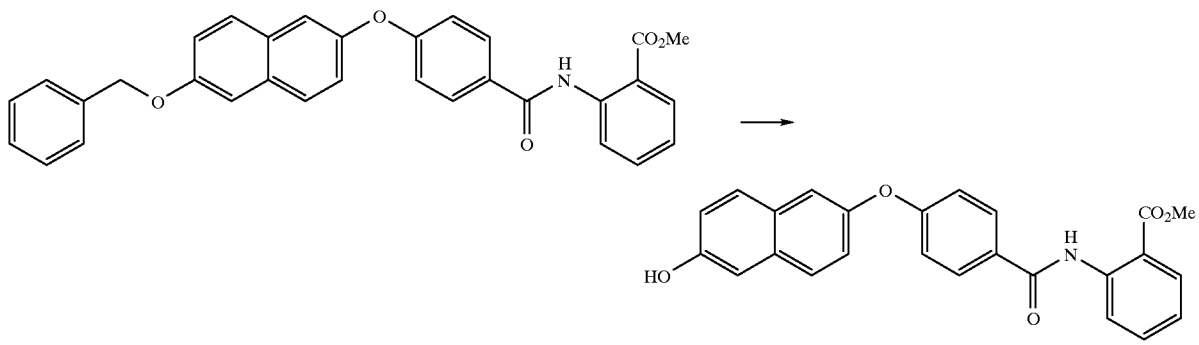

A 1.35 g (2.68 mmol) of 2-(4-(6-benzyloxy-2-naphtyloxy)benzamide)benzoic acid methyl ester (Compound No. 1205) obtained in Example 22 was dissolved in 50 ml of THF, to which was added 630 mg of 10% Pd/C. The system was put in an atmosphere of hydrogen, and stirred at room temperature for 32 hours. The reaction mixture was filtered through a sheet of celite and the filtrate was concentrated to give 1.04 g (94% yield) of 2-(4-(6-hydroxy-2-naphthyloxy)benzamide)benzoic acid methyl ester.

¹H-NMR (CDCl₃) δ (ppm): 3.88(s, 3H), 5.26(br, s, 1H), 6.90–7.20(m, 6H), 7.35(br, s, 1H), 7.50–7.70(m, 3H), 7.90–8.05 (m, 3H), 8.84(d, J=7.6Hz, 1H), 11.95(br, s, 1H).

¹H-NMR (DMSO-d₆) δ (ppm): 7.05–7.20(m, 6H), 7.24(s, 1H), 7.60(dt, J=2.0 and 9.0Hz, 1H), 7.74(dd, J=9.0 and 13.0Hz, 2H), 7.95(d, J=8.9Hz, 2H), 8.03(dd, J=1.7 and 8.0Hz, 1H), 8.28(d, J=9.0Hz, 1H), 9.70(s, 1H), 12.2(br, s, 1H), 13.7(br, s, 1H).

Example 90

Production of 2-(4-(6-hydroxy-2-naphtyloxy)phenylacetiamide)bezoic Acid Methyl Ester (Compound No. 1207)

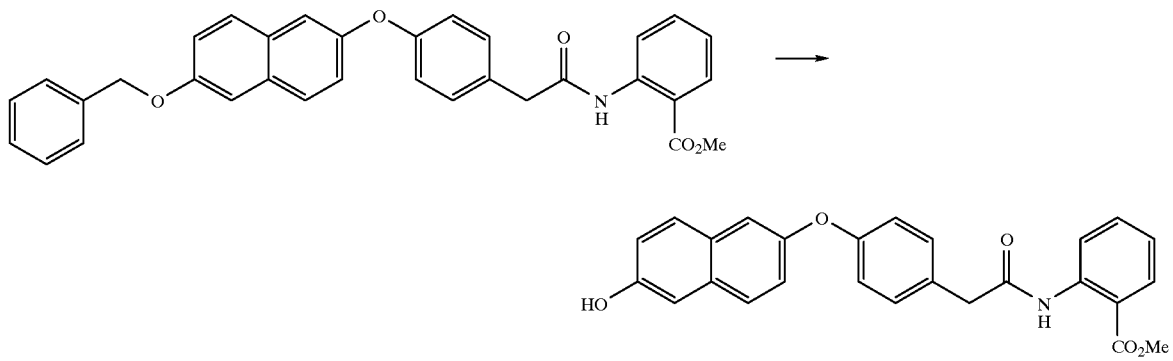

Example 89

Production of 2-(4-(6-hydroxy-2-naphtyloxy)benzamide)benzoic Acid (Compound No. 1202)

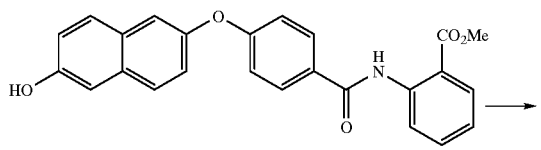

A 1.04 g (2.52 mmol) of 2-(4-(6-hydroxy-2-naphtyloxy)benzamide)benzoic acid methyl ester(Compound No. 1201) obtained in Example 88 was used as a starting material. 0.78 g (yield 78%) of the title compound was prepared according to the procedure in Example 2.

A 50 mg (0.097 mmol) of 2-(4-(6-benzyloxy-2-naphtyloxy)phenylacetamide)benzoic acid methyl ester (Compound No. 1223) obtained in Example 88 was used as a strong material. 22 mg of the title compound was prepared according to the procedure in Example 88 (Yield 53%).

¹H-NMR (CDCl₃) δ (ppm): 3.76(s, 2H), 3.89(s, 3H), 5.26(br, s, 1H), 7.02–7.15(m, 5H), 7.22(dd, J=2.3 and 8.9Hz, 1H), 7.31–7.37(m, 3H), 7.53(dt, J=1.7 and 8.9Hz, 1H), 7.60(d, J=9.2Hz, 1H), 7.64(d, J=8.9Hz, 1H), 8.01(dd, J=1.7 and 8.3Hz, 1H), 8.72(d, J=8.3Hz, 1H), 11.10(br, s, 1H).

Example 91

Production of 2-(4-(6-hydroxy-2-naphtyloxy)phenylacetamide)benzoic Acid (Compound No. 1208)

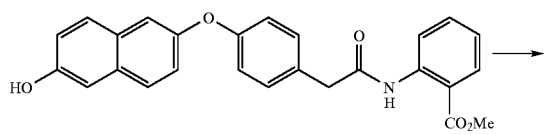

-continued

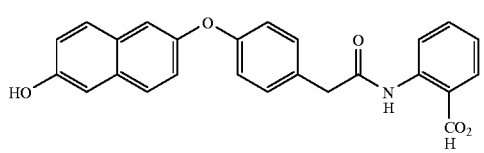

A 22 mg (0.05 mmol) of 2-(4-(6-hydroxy-2-naphtyloxy)phenylacetamide)benzoic acid methyl ester(Compound No. 1207) obtained in Example 90 was used as a starting material. 9 mg of the title compound was prepared according to the procedure in Example 2 (Yield 42%).

$^1$H-NMR (DMSO-d$_6$) δ (ppm): 3.83(s, 2H), 7.07–7.28(m, 6H), 7.41–7.46(m, 3H), 7.65(d, J=7.6Hz, 1H), 7.75(d, J=8.9Hz, 1H), 7.81(d, J=8.9Hz, 1H), 8.04(dd, J=1.3 and 7.9Hz, 1H), 8.59(d, J=8.3Hz, 1H) 9.72(s, 1H), 11.24(br, s, 1H), 13.65(br, s, 1H).

Example 92

In Vitro Inhibition of the Production of Human IgE Antibodies

According to the method described in J. Immunol., 146:1836–1842, 1991 and J. Immunol., 147:8–13, 1991, the concentrations of IgE and IgG antibodies were measured by the procedures described below.

Peripheral venous blood was sampled from the healthy person, and submitted to density-gradient centrifugation to isolate lymphocytes. The lymphocytes thus obtained were washed and suspended in a culture medium (RPMI-1640 (provided by Gibco)+10% heat-inactivated FCS (Whittaker)+100 g/ml streptomycin+100 U/ml penicillin+ 2mM L-glutamine). The cell suspensions were cultured for 1 week in the presence/absence of the compounds of this invention at the concentrations as described in Tables 3-1 to 3-2 together with human interleukin 4 (IL-4, Genzyme)(0.1 mg/ml), anti CD40 antibodies (anti CD40Ab, Biosource, clone B-B20)(2 mg/ml) and human interleukin 10 (IL-10, Genzyme)(0.2 mg/ml). The culture medium was supplied freshly to the cell suspension, and the mixture was further cultured for another week. The supernatant was sampled and the concentrations of IgE and IgG antibodies therein were measured by sandwich ELISA.

The ELISA was based, for the assay of IgE antibodies, on the use of rabbit anti-human IgE( ) antibodies (ICN) as the primary antibody and biotin-linked anti-human IgE monoclonal antibodies (G7-26, PharMingen) as the secondary antibody. For the assay of IgG antibodies, anti-human IgG monoclonal antibodies (G18-145, PharMingen) and biotin-linked donkey anti-human IgG antibodies (H+L)(Jackson) were used for the primary and secondary antibodies, respectively. For the assay of both IgE and IgG antibodies, Avidin-Biotin-Horse Radish Peroxidase (ABC kit, Vector Lab) and TMB (3,3',5,5'-tetramethylbenzidine) microwell peroxidase substrate system (Kirkegaard & Perry Laboratories Inc.) were used as the enzyme and the substrate, respectively. The assays were made by the use of conventionally known ELISA.

The inhibitory effect (%) of a given compound of this invention on the production of the antibody was calculated with respect to the concentration of the same antibody when the compound was not coexistent (refer to Uejima et al., American Academy of Allergy and Immunology, Proceedings of 1995 Annual Meeting, Program No. 818). The results are listed in Tables 3-1 to 3-2.

TABLE 3-1

Inhibitory effect of naphthalene derivatives on antibody production (in vitro)

| Compound No. | Concentration (μM) | Inhibition of antibody production (%) | |
|---|---|---|---|
| | | IgE | IgG |
| 1101 | 3 | 30.3 | −2.8 |
| 1104 | 1 | 35.9 | −4.7 |
| | 3 | 85.6 | −6.2 |
| | 10 | 98.2 | 20.5 |
| 1105 | 3 | 42.4 | −6.4 |
| 1106 | 3 | 42.6 | −25.3 |
| 1107 | 3 | 44.9 | −17.2 |
| 1111 | 3 | 38.0 | 20.0 |
| 1116 | 3 | 93.0 | 36.9 |
| 1118 | 3 | 77.2 | −12.9 |
| 1120 | 3 | 19.9 | 13.6 |
| 1122 | 3 | 59.9 | 9.7 |
| 1123 | 3 | 21.7 | −0.8 |
| 1126 | 1 | 63.9 | −5.0 |
| | 3 | 93.5 | 35.4 |
| | 10 | 97.9 | 84.0 |
| 1148 | 3 | 25.5 | 10.3 |
| 3102 | 3 | 19.9 | −2.8 |
| 3103 | 3 | 41.9 | 3.5 |
| 4103 | 3 | 45.5 | −4.2 |
| 5104 | 3 | 51.4 | 1.6 |
| 7102 | 3 | 15.4 | 5.4 |
| 8102 | 3 | 60.0 | 9.7 |

TABLE 3-2

| Compound No. | Concentration (μM) | Inhibition of antibody production (%) | |
|---|---|---|---|
| | | IgE | IgG |
| 1204 | 3 | 64.0 | −11.4 |
| 1202 | 3 | 76.6 | −8.7 |
| 1206 | 3 | 84.0 | 11.5 |
| 1224 | 3 | 78.6 | 83.2 |
| 1216 | 3 | 84.7 | 19.3 |
| 1214 | 3 | 86.1 | 41.6 |
| 1218 | 3 | 91.4 | 47.8 |
| 1210 | 3 | 92.8 | 59.9 |
| 1212 | 3 | 89.1 | 74.6 |
| 1150 | 3 | 64.4 | 3.3 |
| 1158 | 3 | 57.7 | −5.2 |
| 1160 | 3 | 59.7 | −1.3 |
| 1162 | 3 | 82.1 | −0.3 |
| 1208 | 3 | 86.2 | −8.4 |
| 1220 | 3 | 99.1 | 43.4 |
| 1222 | 3 | 98.9 | 36.6 |
| 1226 | 3 | 98.4 | 50.6 |
| 1228 | 3 | 98.9 | 42.4 |

Tables 3-1 and 3-2 show that the compounds of this invention inhibit the production of IgE antibodies.

This result suggests that the compounds of this invention would be effective as a drug for propylaxis and/or treatment of allergic diseases such as bronchial asthma, allergic rhinitis, allergic conjunctivitis, atopic dermatitis, anaphylactic shocks, mite allergy, pollinosis, food allergy or the like. The inhibitory activity was IgE preferential. This result suggests that the compounds of this invention would not act as an immunosuppressant based on their inhibitory effect on IgG production but would rather act as a drug more selectively prophylactic and/or therapeutic towards allergic diseases.

Example 93

Inhibitory Effects on the TF Production in Human Peripheral Blood Monocytes

Peripheral venous blood was sampled from the healthy person, and submitted to density-gradient centrifugation so that monocytes might be isolated. The monocytes thus obtained were washed with minimum essential medium (MEM, Gibco) and suspended in a culture medium (RPMI-1640(Gibco)+25 mM HEPES buffer+100 μg/ml streptomycin+100 U/ml penicillin G+2 mM L-glutamine) to give a suspension with a density of $1\times10^6$ cells/ml. A 0.15 ml of the cell suspension was placed onto each of the wells of a 96-well microplate, to which the compound of this invention as described in Tables 4-1 to 4-2 was added (0.05 ml of the culture medium), and the assembly was placed for 1 hour in a $CO_2$ incubator for cultivation. Then, LPS (lipopolysaccarides, E. coli 0111B4, Difco) 1 μg/ml was added thereto, and the assembly was further cultured for 16 hours. After the supernatant being removed, the residue was washed with physiological saline, 0.1 ml of 16 mM OG (n-octyl-β-D-glucopyranoside) was added thereto, and the assembly was stirred to make TF soluble. A 0.2 ml of physiological saline was added to each residue (final dilution was 1.5 fold) and this preparation was used for determination of the coagulation stimulating activity (TF-like activity). The test compound had been dissolved in DMSO to give a 0.1 M solution which was diluted with the culture medium prior to use. The final concentration of DMSO was 0.01% or less.

To each well of the microplate, 50 μl of human plasma and 50 μl of the test sample prepared as above for determination of the coagulation stimulating activity, or 50 μl of standard thromboplastin (human thromboplastin, Thromborel S, Behringwerke) were added. The microplate was incubated at 37° C. for 5 minutes, to which was added 25 mM $CaCl_2$ (50 μl/well) containing phosphorous lipids (Platelin, Organon Teknica) at a concentration of 100 μl/ml to initiate coagulation. Coagulation was determined on the basis of absorption at 540 nm, and the measurement lasted 7 to 20 minutes. The data were analyzed with a data analyzing software SOFTMax (Molecular Devices) and the maximum rate time was taken as the coagulation time. The logarithmic values of the coagulation times and standard thromboplastin concentrations are plotted, and a regression parabola was drawn among the dots to give a test curve. From the curve, the inhibitory effect (%) of a given test compound on TF production was calculated. (Refer to J. Imnmunol. Methods, 133:21–29, 1990, and Proc. Natl. Acad. Sci. USA, 89:10370–10374, 1992).

The results are shown in Tables 4-1 to 4-2.

TABLE 4-1

Inhibitory effect of naphthalene derivatives on TF production by monocytes in human peripheral blood

| Compound No. | Concentration (μM) | Inhibition of TF production (%) |
|---|---|---|
| 1104 | 1 | 45.3 |
|  | 3 | 90.4 |
|  | 10 | 100.0 |
| 3102 | 3 | 100.0 |
| 4103 | 1 | 16.5 |
|  | 3 | 74.4 |
|  | 10 | 100.0 |
| 7102 | 3 | 10.6 |

TABLE 4-1-continued

Inhibitory effect of naphthalene derivatives on TF production by monocytes in human peripheral blood

| Compound No. | Concentration (μM) | Inhibition of TF production (%) |
|---|---|---|
|  | 10 | 81.1 |
| 5102 | 1 | 19.8 |
|  | 3 | 74.1 |
|  | 10 | 99.9 |
| 6102 | 3 | 75.8 |
|  | 10 | 100.0 |
| 1148 | 3 | 92.9 |
| 1109 | 1 | 74.9 |
|  | 3 | 99.4 |
|  | 10 | 99.7 |
| 1111 | 1 | −9.0 |
|  | 3 | 96.2 |
|  | 10 | 100.0 |
| 1113 | 1 | 25.3 |
|  | 3 | 83.6 |
|  | 10 | 100.0 |

TABLE 4-2

| Compound No. | Concentration (μM) | Inhibition of TF production (%) |
|---|---|---|
| 1116 | 3 | 96.6 |
| 1118 | 3 | 86.9 |
| 1126 | 3 | 26.5 |
| 1146 | 3 | 23.5 |
| 1202 | 3 | 33.4 |
| 1204 | 1 | 75.7 |
|  | 3 | 100.0 |
|  | 10 | 100.0 |
| 3103 | 3 | 77.9 |
| 3104 | 3 | 96.9 |

Tables 4-1 to 4-2 reveals that the compounds of this invention inhibit the TF production.

This result suggests that the compounds of this invention would be effective as a drug for prophylaxis and/or treatment of the diseases that are associated with enhanced production or activity of TF such as infections, delayed immune response, autoimmune diseases like SLE, rejection reactions associated with transplantation of various organs, glomerular nephritis, various thromboses associated with viral hepatitis or the like, occlusive arteriosclerosis, cerebral embolism, cerebral infarction, pulmonary embolism, pulmonary infarction, angina pectoris, myocardial infarction, restenosis, Buerger disease, diseases involved in hypertrophic endometritis, and turbidity of an artificial crystalline lens embedded for the treatment of cataract.

Example 94

In Vivo Inhibition of Mice IgG Production

TNP-KLH (trinitrophenyl-keyhole-lymphet-hemocyanin) was prepared by the method as described in J. Immunol., 97:421–430, 1966 from KLH and trinitrobenzene sulfonic acid. A 0.5 g of TNP-KLH suspended in 0.2 ml of saline and 1 mg of aluminum hydroxide gel were injected into the peritoneal cavity of BDF1 mice (8 weeks old) for immunization. From the day of immunization onward, the compound of this invention listed in Table 5 was given subcutaneously to the same animal twice a day for 10 days (100 mg/kg/day, dissolved in 0.5% Tween 80 in saline, and N=10). To the control group, 0.5% Tween 80 in saline was given at the same time schedule (N=10). Ten days after immunization, blood was extracted from the heart, and the concentrations of IgE, $IgG_1$ and IgM antibodies were determined by ELISA (Immunol. Lett., 23:251–256, 1990, and Eur. J. Immunol., 20:2499–2503, 1990). Inhibition (%) of the antibody production with respect to the control was calculated. The results are listed in Table 5.

TABLE 5

Inhibitory effect of naphthalene derivatives on antibody production (in vivo)

| Compound No. | Inhibition of antibody production (%) | | |
|---|---|---|---|
| | IgE | $IgG_1$ | IgM |
| 1104 | 60.4 | 24.4 | 56.1 |
| 1126 | 78.9 | 46.8 | 70.2 |

Table 5 reveals that the compounds of this invention have an in vivo strong inhibitory effect on the antibody production towards IgE, IgM and $IgG_1$ in this order.

This result suggests that the compounds of this invention would be effective as a drug for prophylaxis and/or treatment of allergic diseases such as bronchial asthma, allergic rhinitis, allergic conjunctivitis, atopic dermatitis, anaphylactic shocks, mite allergy, pollinosis, food allergy, urticaria, ulcerative colitis, eosinophilic gastroenteritis or the like.

Example 95

Inhibition of Histamine Release from Rat Mast Cells

A 1 ml of anti-DNP-Ascaris (Didets) anti-serum (prepared as described in J. Immunol., 106:1002, 1971) was injected into the peritoneal cavity of 5 SD strain rats of 7 weeks old. Forty eight hours later, the animals were bled to death, and 20 ml of HBSS (Hanks balanced salt solution) was injected into their peritoneal cavity. After about 90 second massaging, the HBSS washing was recovered, and cells released into the peritoneal cavity were collected from the washing. The ascitic cells thus collected were washed once with 0.1% BSA/Tyrode-HEPES, and then resuspended in 0.1% BSA/Tyrode-HEPES to give a suspension with a density of $5\times10^6$ cells/ml. The cell suspension was incubated at 37° C. for 10 minutes in the presence/absence of a test substance, that is, the compound listed in Table 6.

To the resulting mixture was added a histamine releasing agent (20 μg/ml of DNP-Ascaris (DNP-As) (Didets)+25 μg/ml of phosphatidylserine (PS) or 0.2 μg/ml of calcium ionophore A23187), and the reaction was allowed to proceed at 37° C. for 20 minutes. Then, the cell suspension was centrifuged to obtain supernatant. Histamine released in the supernatant was determined by the fluorescent method (J. Pharmacol. Exp. Ther. 127:182, 1959). Inhibitory effect (%) of a given compound of this invention on histamine release was calculated relative to the histamine release when the compound was not coexistent. The results are shown in Table 6.

TABLE 6

Inhibitory effect of naphthalene derivatives on histamine release from mast cells of the rat

| Histamine release agent | Compound No. | Concentration (μM) | Inhibiton of histamine release (%) |
|---|---|---|---|
| DNP-As + PS | 1104 | 10 | 42.7 |
| | | 100 | 84.2 |
| | 1126 | 10 | 25.4 |
| | | 100 | 90.2 |
| A23187 | 1104 | 10 | 75.4 |
| | | 100 | 78.0 |
| | 1126 | 10 | 54.2 |
| | | 100 | 79.8 |

Table 6 reveals that the compounds of this invention inhibit histamine release from rat mast cells.

This result suggests that the compounds of this invention would be effective as a drug for prophylaxis and/or treatment of allergic diseases such as bronchial asthma, allergic rhinitis, allergic conjunctivitis, atopic dermatitis, anaphylactic shocks, mite allergy, pollinosis, food allergy, urticaria, ulceative colitis, eosinophilic gastroenteritis or the like.

Example 96

Inhibition of Histamine Release from Human Basophils

To human heparinized peripheral blood was added 1/10 volume of 6% Dextran 500 in saline, and the mixture was allowed to stand at room temperature for 1 hour, to isolate a plasma layer containing leukocytes. The leukocytes were separated by centrifugation, washed with PIPE-A (119 mM NaCl, 5 mM KCl, 25 mM PIPES, 40 mM NaOH, 5.6 mM glucose, and 0.03% human serum albumin), and suspended in PIPES-ACM (PIPES A, 1 mM $CaCl_2$ and 0.4 mM $MgCl_2$) to give a cell suspension of a density of $4\times10^6$ cells /ml. To this cell suspension was added the compound of this invention listed in Table 7 as a test drug (0.1 M solution of the compound in DMSO was diluted with PIPES-ACM to give a 10 M solution), or the cell suspension was left untouched. After 30 second, calcium ionophore A23187 (0.2 g/ml) was added. The reaction was allowed to proceed at 37 for 45 minutes. The resulting mixture was centrifuged to isolate a supernatant. Histamine release in the supernatant was determined by the fluorescent method. Inhibitory effect (%) of a given compound of this invention on histamine release was calculated relative to the histamine release when the compound was not coexistent(refer to Allergy, 37:313–321, 1988). The results are shown in Table 7.

TABLE 7

Inhibitory effect of naphthalene derivatives on histamine release from human basophils

| Compound No. | Inhibition of histamine release (%) |
|---|---|
| 1104 | 20.4 |
| 1126 | 55.8 |

Table 7 reveals that the compounds of this invention inhibit histamine release from human basophils.

This result suggests that the compounds of this invention would be effective as a drug for prophylaxis and/or treatment of allergic diseases such as urticaria, ulcerative colitis, eosinophilic colitis, bronchial asthma, allergic rhinitis, allergic conjunctivitis, atopic dermatitis, anaphylactic shocks, mite allergy, pollinosis, food allergy, or the like.

Example 97

Inhibition of Leukotrien $B_4$ ($LTB_4$) Production

The basophils from rats of RBL-1 line (Dainippon Pharmaceutical Co.) cultured on DMEM (Dulbecco's modified Eagle medium) containing 10% FCS suspended in 10 mM HEPES-NaOH buffer (pH 7.4), 90 mM NaCl, 3.7 mM KCl, 0.9 mM $CaCl_2$, 5.6mM glucose, and the compound of this invention listed in Table 8 as a test drug, to give a suspension of a density of $2\times10^6$ cells/ml. The suspension was allowed to stand at 37 for 5 minutes, and calcium ionophores A23187 were added thereto in such a manner that the concentration of 5 M was obtained in the end. The reaction was allowed to proceed at 37 for 10 minutes, and the supernatant was sampled for the ELISA assay (Cayman Chemical, Catalog No. 520111, and J. Immunol., 119:618–622, 1977) of leukotrien $B_4$ ($LTB_4$). IC50 of a given compound of this invention for inhibition of leukotrien production was calculated relative to the production of $LTB_4$ when the compound was not coexistent.

The results are shown in Table 8.

TABLE 8

Inhibitory effect of naphthalene derivatives on leukotrien $B_4$ ($LTB_4$) production

| Compound No. | $IC_{50}$ ($\mu M$) |
|---|---|
| 1104 | 0.21 |
| 1126 | 0.60 |

Table 8 reveals that the compounds of this invention inhibit the $LTB_4$ production. This result suggests that the compounds of this invention would be effective as a drug for prophylaxis and/or treatment of allergic diseases such as urticaria, ulcerative colitis, eosinophilic gastroenteritis, bronchial asthma, allergic rhinitis, allergic conjunctivitis, atopic dermatitis, anaphylactic shocks, mite allergy, pollinosis, food allergy, or the like.

Furthermore, Examples 92 and 94–97 demonstrated that the compounds of this invention have an inhibitory effect on IgE production, histamine release and $LTB_4$ production, suggesting that they would be effective as a drug for prophylaxis and/or treatment of allergic diseases not only because of their inhibitory action on IgE production, but also because of their suppressing effects on chemical mediators, such as histamine and $LTB_4$.

Example 98

Preparation of Tablets

From the compounds of this invention were made tablets each of which contains the following as ingredients.

| | |
|---|---|
| Compound No. 1104 | 50 mg |
| Lactose | 230 mg |
| Potato starch | 80 mg |
| Polyvinylpyrrolidone | 11 mg |
| Magnesium stearate | 5 mg |

The compound of this invention (Compound No. 1104), lactose and potato starch were mixed, and wetted evenly with 20% solution of polyvinylpyrrolidone in ethanol. The resulting mass was strained with a 20 nm mesh, dried at 45° C., and strained again with a 15 nm mesh. The granules thus obtained were mixed with magnesium stearate, and compacted into tablets.

FIELD OF INDUSTRIAL UTILITY

This invention provides naphthalene derivatives capable of, for example, inhibiting the production of IgE antibodies and of TF. Inhibitory activity on IgE production is especially attractive in view of IgE selectivity, potency, and low toxicity. Accordingly, the compounds of this invention would be effective for prophylaxis and treatment of allergic diseases involved in the augmented production of IgE antibodies such as certain bronchial asthma, conjunctivitis, rhinitis, dermatitis, hypersensitivity or the like, and of the diseases resulting from the augmented production/activity of TF.

We claim:

1. A naphthalene derivative having the following formula (I):

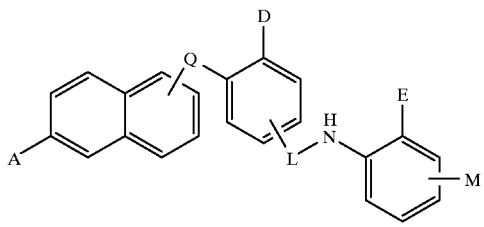

wherein A represents a hydrogen atom, a hydroxy group, a $C_7$–$C_{11}$ aralkyloxy group, or an alkoxy group composed of an oxy group and a $C_1$–$C_{12}$ aliphatic or alicyclic, saturated or unsaturated hydrocarbon group in which the alkyl moiety may be substituted with a $C_6$–$C_{10}$ aryloxy group;

O represents O, S, O—$CH_2$, S—$CH_2$, or $CHOR^1$;

L represents CO, $CR^2R^3CO$, $CH_2CH_2CO$, or CH=CHCO;

D represents a hydrogen atom, $NO_2$, $NH_2$, $CO_2R^4$, or a group having the following formula (II):

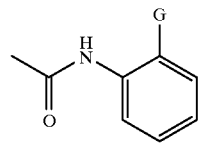

wherein G represents a hydrogen atom, OH, $SO_2NH_2$, $CO_2R^6$, CN or a tetrazol-5-yl group;

E represents a hydrogen atom, OH, $SO_2NH_2$, $CO_2R^5$, CN, or a tetrazol-5-yl group;

M represents a hydrogen atom, a $C_1$–$C_4$ lower alkyl group, a nitro group, or a halogen atom; and $R^1$, $R^2$, $R^3$, $R^4$, $R^5$ and $R^6$, independently represent a hydrogen atom or a $C_1$–$C_4$ lower alkyl group;

a pharmacologically acceptable salt thereof or a pharmacologically acceptable solvate thereof.

2. The naphthalene derivative according to claim 1 wherein E represents $CO_2R^5$ where $R^5$ represents a hydrogen atom or a $C_1$–$C_4$ lower alkyl group or a tetrazol-5-yl group, the pharmacologically acceptable salt or the pharmacologically acceptable solvate thereof.

3. The naphthalene derivative according to claim 1 wherein D represents a hydrogen atom, $NO_2$, $NH_2$ or a group represented by formula (II) wherein G represents a hydrogen atom or $CO_2R^6$, and $R^6$ represents a hydrogen atom or a $C_1$–$C_4$ lower alkyl group, the pharmacologically acceptable salt thereof or the pharmacologically acceptable solvate thereof.

4. The naphthalene derivative according to claim 1, wherein D represents a hydrogen atom or $NO_2$, E represents $CO_2R^5$, and $R^5$ represents a hydrogen atom or a $C_1$–$C_4$ lower alkyl group, the pharmacologically acceptable salt or the pharmacologically acceptable solvate thereof.

5. The naphthalene derivatives according to claim 1 wherein M is a hydrogen atom, a methyl group, an ethyl group, a nitro group, a fluorine atom or a chlorine atom, the pharmacologically acceptable salt or the pharmacologically acceptable solvate thereof.

6. The naphthalene derivatives according to claim 1, wherein $R^1$–$R^6$ represent, independently a hydrogen atom or a methyl group, the pharmacologically acceptable salt or the pharmacologically acceptable solvate thereof.

7. The naphthalene derivative according to any one claim of claims 1–6, wherein O represents O, S, O—$CH_2$, S—$CH_2$, or $CHOR^1$ where $R^1$ represents a hydrogen atom or a $C_1$–$C_4$ lower alkyl group and L represents CO, $CR^2R^3CO$ or CH=CHCO where $R^2$ and $R^3$, independently represent a hydrogen atom or a $C_1$–$C_4$ lower alkyl group, the pharmacologically acceptable salt or the pharmacologically acceptable solvate thereof.

8. The naphthalene derivative according to any one claim of claims 1–6, wherein O represents O, S, or $CHOR^1$ where $R^1$ represents a hydrogen atom or a $C_1$–$C_4$ lower alkyl group and L represents CO or $CR^2R^3CO$ where $R^2$ and $R^3$, independently represent a hydrogen atom or a $C_1$–$C_4$ lower alkyl group, the pharmacologically acceptable salt or the pharmacologically acceptable solvate thereof.

9. The naphthalene derivative according to any one claim of claims 1–6, wherein O represents O and L represents CO or $CR^2R^3CO$ where $R^2$ and $R^3$, independently are a hydrogen atom or a $C_1$–$C_4$ lower alkyl group, the pharmacologically acceptable salt or the pharmacologically acceptable solvate thereof.

10. The naphthalene derivative according to any one claim of claims 1–6, wherein O represents O, S, O—$CH_2$ or S—$CH_2$ and L represents CO or CH=CHCO, the pharmacologically acceptable salt or the pharmacologically acceptable solvate thereof.

11. The naphthalene derivative according to any one claim of claims 1–6, wherein O represents O, S, O—$CH_2$ or S—$CH_2$, and L represents CO, the pharmacologically acceptable salt or the pharmacologically acceptable solvate thereof.

12. The naphthalene derivatives according to any one claim of claims 1–6, wherein O represents O, and L represents CH=CHCO, the pharmacologically acceptable salt or the pharmacologically acceptable solvate thereof.

13. The naphthalene derivatives according to claim 1, wherein A represents a hydrogen atom; a hydroxy group; an alkoxy group composed of an oxy group and a $C_1$–$C_{12}$ aliphatic or alicyclic, a saturated hydrocarbon group or a $C_3$–$C_{10}$ aliphatic unsaturated hydrocarbon group, which can be substituted by a phenyloxy group; a benzyloxy group; a phenylpropyloxy group; or a naphtylmethyloxy group, the pharmacologically acceptable salt or the pharmacologically acceptable solvate thereof.

14. The naphthalene derivative according to any one claim of claims 1–12, wherein the substitution by O on the naphthalene ring is at the 2-position of the ring, the pharmacologically acceptable salt or the pharmacologically acceptable solvate thereof.

15. The naphthalene derivative according to any one claim of claims 1–12, wherein substitution by O, L and D are on the benzene ring and the relative position of O and L is para, the pharmacologically acceptable salt or the pharmacologically acceptable solvate thereof.

16. A pharmaceutical composition comprising the naphthalene derivatives as described in claim 1, the pharmacologically acceptable salt or the pharmacologically acceptable solvate thereof and a pharmaceutically acceptable carrier.

17. The pharmaceutical composition according to claim 16, wherein the pharmaceutical composition is as a drug for treating an allergic disease based on an inhibitory action on the production of IgE antibodies.

18. The pharmaceutical composition according to claim 17, wherein the allergic disease is bronchial asthma, allergic rhinitis, allergic conjunctivitis, atopic dermatitis, anaphylactic shocks, mite allergy, pollinosis or food allergy.

19. The pharmaceutical composition according to claim 16, wherein the pharmaceutical composition is effective for the treatment of disease caused by augmented production or activity of TF.

20. The pharmaceutical composition according to claim 19, wherein the disease is DIC; thrombosis; occlusive arteriosclerosis; cerebral embolism; cerebral infarction; pulmonary embolism; pulmonary infarction; angina pectoris; myocardial infarction; restenosis; Buerger disease; diseases involved in hypertrophic endometritis; and turbidity of an artificial crystalline lens embedded for the treatment of cataract.

21. A medicine effective as a prophylactic and/or therapeutic for an allergic disease because of its inhibitory effect on the production of IgE antibody containing a napththalene derivative of claim 1, the pharmacologically acceptable salt or the pharmacologically acceptable solvate as an active ingredient(s).

22. The medicine effective as a prophylactic and/or therapeutic for an allergic disease according to claim 21 being more selectively inhibitory against the production of IgE antibody than against IgG antibody.

23. The medicine effective as a prophylactic and/or therapeutic for a disease resulting from enhanced production or activity of TF containing a naphthalene derivative of claim 1, the pharmacologically acceptable salt or the pharmacologically acceptable solvate as an active ingredient(s).

24. A naphthalene derivative having the following formula (I):

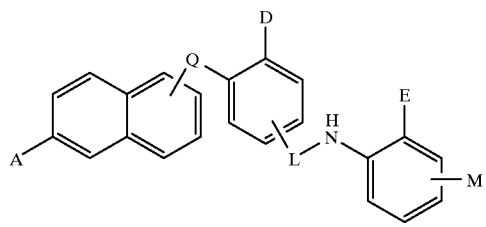

wherein A represents a hydroxy group, a $C_7$–$C_{11}$, aralkyloxy group, or an alkoxy group composed of an oxy group and a $C_1$–$C_{12}$ aliphatic or alicyclic, saturated or unsaturated hydrocarbon group which the alkyl moiety may be substituted with a $C_6$–$C_{10}$ aryloxy group;

Q represents O, S, O—CH$_2$, S—CH$_2$, or CHOR$_1$;

L represents CO, CR$^2$R$^3$CO, CH$_2$CH$_2$CO, or CH=CHCO;

D represents a hydrogen atom, NO$_2$, NH$_2$, CO$_2$R$^4$, or a group having the following formula (II):

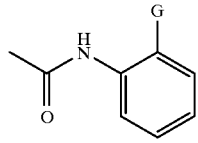

[II]

wherein G represents a hydrogen atom, OH, SO$_2$NH$_2$, CO$_2$R$^6$, CN or a tetrazol-5-yl group;

E represents a hydrogen atom, OH, SO$_2$NH$_2$, CO$_2$R$^5$, CN, or a tetrazol-5-yl group;

M represents a hydrogen atom, a C$_1$–C$_4$ lower alkyl group, a nitro group, or a halogen atom; and R$^1$, R$^2$, R$^3$, R$^4$, R$^5$ and R$^6$, independently represent a hydrogen atom or a C$_1$–C$_4$ lower alkyl group;

a pharmacologically acceptable salt thereof or a pharmacologically acceptable solvate thereof.

* * * * *